United States Patent
Sugiyama et al.

(10) Patent No.: US 7,462,635 B2
(45) Date of Patent: Dec. 9, 2008

(54) THIAZOLE AND OXAZOLE VDAC REGULATOR

(75) Inventors: Yasuo Sugiyama, Kawanishi (JP); Masatoshi Hazama, Ikeda (JP); Norihisa Iwakami, Nishinomiya (JP)

(73) Assignees: Takeda Pharmaceutical Company Limited, Osaka (JP); Tokyo Institute of Technology, Tokyo (JP)

( * ) Notice: Subject to any disclaimer, the term of this patent is extended or adjusted under 35 U.S.C. 154(b) by 0 days.

(21) Appl. No.: 10/507,731

(22) PCT Filed: Mar. 13, 2003

(86) PCT No.: PCT/JP03/02996

§ 371 (c)(1),
(2), (4) Date: Sep. 14, 2004

(87) PCT Pub. No.: WO03/075923

PCT Pub. Date: Sep. 18, 2003

(65) Prior Publication Data

US 2005/0234116 A1 Oct. 20, 2005

(30) Foreign Application Priority Data

Mar. 14, 2002 (JP) ............................... 2002-070754

(51) Int. Cl.
*A61K 31/422* (2006.01)
*A61K 31/427* (2006.01)
*A61K 31/4178* (2006.01)

(52) U.S. Cl. ..................... 514/377; 514/365; 514/397

(58) Field of Classification Search ................. 514/377, 514/397, 365; 548/235, 233, 311.1, 335.1
See application file for complete search history.

(56) References Cited

U.S. PATENT DOCUMENTS

| 5,464,847 | A | 11/1995 | Courtemanche et al. |
| 6,605,629 | B1 * | 8/2003 | Momose et al. ............. 514/374 |
| 2002/0010195 | A1 | 1/2002 | Ghosh et al. |

FOREIGN PATENT DOCUMENTS

EP 0 560 136 A1 9/1993

JP 2000-287689 A 10/2000

OTHER PUBLICATIONS

Thompson et al., Science vol. 267, Mar. 10, 1995, pp. 1456-1462.*
Shimizu et al., "Essential Role of Voltage-Dependent Anion Channel in Various Forms of Apoptosis in Mammalian Cells," The Journal of Cell Biology, vol. 152, No. 2, Jan. 22, 2001, pp. 237-250.
Sampson et al., "The Murine Voltage-dependent Anion Channel Gene Family", The Journal of Biological Chemistry, Vo. 272, No. 30, pp. 18966-18973.
Thompson, "Apoptosis in the Pathogenesis and Treatment of Disease", Science vol. 267, Mar. 10, 1995, pp. 1456-1462.
Yoo et al., "Changes of voltage-dependent anion-selective channel proteins VDAC1 and VDAC2 brain levels in patients with Alzheimer's disease and Down Syndrome", Electrophoresis 2001, 22, pp. 172-179.
Shimizu et al., "Bcl-2 family proteins regulate the release of apoptogenic cytochrome c by the mitochondrial channel VDAC", Nature, vol. 399, Jun. 3, 1999, pp. 483-487.
Kogaku, Players That Regulate Apoptosis, VDAC, Functional Target of Gcl-2 Family, Cell Technology, Vo. 18, No. 12, 1999, pp. 1765-1772 (English Translation Attached—14 pages).
Wong et al. "The Friedreich's ataxia mutation confers cellular sensitivity to oxidant stress which is rescued by chelators of iron and calcium and inhibitors of apoptosis", Human Molecular Genetics, 1999, Vo. 8, No. 3 pp. 425-430.

* cited by examiner

Primary Examiner—Joseph McKane
Assistant Examiner—Yong Chu
(74) Attorney, Agent, or Firm—Foley & Lardner LLP (57) ABSTRACT

The present invention provides a VDAC regulator comprising a compound represented by the formula (I):

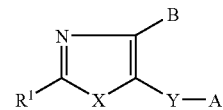

wherein $R^1$ is a halogen atom, an optionally substituted heterocyclic group, an optionally substituted hydroxyl group, an optionally substituted thiol group or an optionally substituted amino group; A is an optionally substituted acyl group, an optionally substituted heterocyclic group, an optionally substituted hydroxyl group or an optionally esterified or amidated carboxyl group; B is an optionally substituted aromatic group; X is an oxygen atom, a sulfur atom or an optionally substituted nitrogen atom; and Y is a divalent hydrocarbon group or heterocyclic group; a salt thereof or a prodrug thereof, which is useful as an agent for the prophylaxis or treatment of Down's syndrome and the like.

8 Claims, 2 Drawing Sheets

THIAZOLE AND OXAZOLE VDAC REGULATOR

This application is a National Phase Application of application No. PCT/JP03/002996, filed Mar. 13, 2003, published in a non-English language, which claims priority to Japanese application 2002-70754, filed Mar. 14, 2002. The entire contents of each of the aforementioned applications are incorporated herein by reference.

TECHNICAL FIELD

The present invention relates to a VDAC regulator, apoptosis suppressor or mitochondria function ameliorator useful as an agent for the prophylaxis or treatment of Down's syndrome and the like.

The present invention also relates to a method for screening an agent for the prophylaxis or treatment of a nervous system disease.

BACKGROUND ART

VDAC, that is, the Voltage-dependent Anion Channel, is also called mitochondria porin and plays an important role in the energy metabolism regulation of mitochondria in eukaryotic cells. Also, VDAC is known to play an essential role in cytochrome c leakage from mitochondria and apoptosis in mammalian cells (The Journal of Cell Biology, Volume 152, pp. 237-250 (2001)).

In the meantime, the compound represented by the formula (I), which is used as the active ingredient in the present invention, is described as a neurotrophin production/secretion promoter in WO01/14372.

However, there is no report that this compound is used as a VDAC regulator, apoptosis suppressor or mitochondria function ameliorator.

DISCLOSURE OF THE INVENTION

An objective of the present invention is to provide a VDAC regulator, apoptosis suppressor or mitochondria function ameliorator useful as an agent for the prophylaxis or treatment of Down's syndrome and the like.

Another object of the present invention is to provide a method for screening an agent for the prophylaxis or treatment of a nervous system disease.

The present inventors studied in search of a VDAC regulator, apoptosis suppressor or mitochondria function ameliorator and found that a compound represented by the formula (I):

wherein $R^1$ is a halogen atom, an optionally substituted heterocyclic group, an optionally substituted hydroxy group, an optionally substituted thiol group or an optionally substituted amino group; A is an optionally substituted acyl group, an optionally substituted heterocyclic group, an optionally substituted hydroxy group or an optionally esterified or amidated carboxyl group; B is an optionally substituted aromatic group; X is an oxygen atom, a sulfur atom or an optionally substituted nitrogen atom; and Y is a divalent hydrocarbon group or heterocyclic group [hereinafter sometimes abbreviated as Compound (I)] possesses excellent VDAC-regulating action, apoptosis-suppressing action and mitochondria function-ameliorating action, which resulted in the completion of the present invention.

Accordingly, the present invention relates to 1) a VDAC regulator comprising Compound (I), a salt thereof or a prodrug thereof;
2) the agent of the aforementioned 1), wherein $R^1$ is an optionally substituted heterocyclic group;
3) the agent of the aforementioned 1), wherein $R^1$ is an optionally substituted 5-membered nitrogen-containing aromatic heterocyclic group;
4) the agent of the aforementioned 1), wherein $R^1$ is an optionally substituted imidazolyl group;
5) the agent of the aforementioned 1), wherein A is an optionally substituted hydroxy group;
6) the agent of the aforementioned 1), wherein B is an optionally substituted phenyl group;
7) the agent of the aforementioned 1), wherein X is an oxygen atom;
8) the agent of the aforementioned 1), wherein Y is a divalent aliphatic hydrocarbon group;
9) the agent of the aforementioned 1), wherein Compound (I) is 4-(4-chlorophenyl)-2-(2-methyl-1-imidazolyl)-5-[3-(2-methylphenoxy)propyl]oxazole;
10) an apoptosis suppressor comprising Compound (I), a salt thereof or a prodrug thereof;
11) an agent for the prophylaxis or treatment of Down's syndrome comprising a VDAC regulator;
12) the agent of the aforementioned 11), wherein the VDAC regulator is Compound (I), a salt thereof or a prodrug thereof;
13) a method for screening an agent for the prophylaxis or treatment of a nervous system disease, which comprises using VDAC;
14) the method for screening of the aforementioned 13), which comprises determining binding ability of a test compound to VDAC;
15) the method for screening of the aforementioned 13), which comprises comparing a VDAC function between in the presence and in the absence of a test compound;
16) the method for screening of the aforementioned 13), wherein the nervous system disease is diabetic neuropathy;
17) the method for screening of the aforementioned 13), wherein the nervous system disease is amyotrophic lateral sclerosis;
18) a method for regulating VDAC in a mammal, which comprises administering Compound (I), a salt thereof or a prodrug thereof to said mammal;
19) use of Compound (I), a salt thereof or a prodrug thereof for the production of a VDAC regulator;
20) a method for suppressing apoptosis in a mammal, which comprises administering Compound (I), a salt thereof or a prodrug thereof to said mammal;
21) use of Compound (I), a salt thereof or a prodrug thereof for the production of an apoptosis suppressor;
22) a method for preventing or treating Down's syndrome in a mammal, which comprises administering a VDAC regulator to said mammal;
23) use of a VDAC regulator for the production of an agent for the prophylaxis or treatment of Down's syndrome;
24) a method for preventing or treating a nervous system disease in a mammal, which comprises administering a VDAC regulator to said mammal;
25) the method of the aforementioned 24), wherein the nervous system disease is diabetic neuropathy;

26) the method of the aforementioned 24), wherein the nervous system disease is amyotrophic lateral sclerosis;
27) a mitochondria function ameliorator comprising Compound (I), a salt thereof or a prodrug thereof;
28) use of Compound (I), a salt thereof or a prodrug thereof for the production of a mitochondria function ameliorator;
29) a method for ameliorating mitochondria function in a mammal, which comprises administering Compound (I), a salt thereof or a prodrug thereof to said mammal; and the like.

BEST MODES FOR EMBODIMENT OF THE INVENTION

Referring to the formula (I), as examples of the "halogen atom" represented by $R^1$, fluorine, chlorine, bromine and iodine can be mentioned. Particularly preferred are fluorine and chlorine.

Referring to the formula (I), as the heterocyclic group of the "optionally substituted heterocyclic group" represented by $R^1$, a 5- or 6-membered ring containing 1 to 4 atoms selected from a nitrogen atom, an oxygen atom and a sulfur atom as ring-constituting atoms in addition to carbon atoms, and a condensed ring thereof can be mentioned. As examples of the condensed ring, a condensed ring comprising such a 5- or 6-membered ring and a 6-membered ring containing 1 or 2 nitrogen atoms, a benzene ring, or a 5-membered ring containing one sulfur atom, can be mentioned.

As specific examples of the heterocyclic group, aromatic heterocyclic groups such as pyridyl (e.g., 2-pyridyl, 3-pyridyl, 4-pyridyl and the like), pyrimidinyl (e.g., 2-pyrimidinyl, 5-pyrimidinyl, 6-pyrimidinyl and the like), pyridazinyl (e.g., 3-pyridazinyl, 4-pyridazinyl and the like), pyrazinyl (e.g., 2-pyrazinyl and the like), pyrrolyl (e.g., 1-pyrrolyl, 2-pyrrolyl and the like), imidazolyl (e.g., 1-imidazolyl, 2-imidazolyl, 4-imidazolyl, 5-imidazolyl and the like), pyrazolyl (e.g., 1-pyrazolyl, 3-pyrazolyl, 4-pyrazolyl and the like), isoxazolyl, isothiazolyl, thiazolyl (e.g., 2-thiazolyl, 4-thiazolyl, 5-thiazolyl and the like), oxazolyl (e.g., 2-oxazolyl, 4-oxazolyl, 5-oxazolyl and the like), 1,2,4-oxadiazolyl (e.g., 1,2,4-oxadiazol-5-yl and the like), 1,2,4-triazolyl (e.g., 1,2,4-triazol-1-yl, 1,2,4-triazol-3-yl and the like), 1,2,3-triazolyl (e.g., 1,2,3-triazol-2-yl, 1,2,3-triazol-4-yl and the like), tetrazolyl (e.g., tetrazol-1-yl, tetrazol-5-yl and the like), benzimidazolyl (e.g., benzimidazol-1-yl, benzimidazol-2-yl and the like), indolyl (e.g., indol-1-yl, indol-3-yl and the like), 1H-indazolyl (e.g., 1H-indazol-1-yl and the like), 1H-pyrrolo[2,3-b]pyrazinyl (e.g., 1H-pyrrolo[2,3-b]pyrazin-1-yl and the like), 1H-pyrrolo[2,3-b]pyridyl (e.g., 1H-pyrrolo[2,3-b]pyridin-1-yl and the like), 1H-imidazo[4,5-b]pyridyl (e.g., 1H-imidazo[4,5-b]pyridin-1-yl and the like), 1H-imidazo[4,5-c]pyridyl (e.g., 1H-imidazo[4,5-c]pyridin-1-yl and the like), 1H-imidazo[4,5-b]pyrazinyl (e.g., 1H-imidazo[4,5-b]pyrazin-1-yl and the like), benzotriazolyl and the like; and non-aromatic heterocyclic groups such as pyrrolidinyl (e.g., 1-pyrrolidinyl and the like), piperidyl (e.g., 1-piperidyl and the like), morpholinyl (e.g., morpholin-4-yl and the like), thiomorpholinyl (e.g., thiomorpholin-4-yl and the like), piperazinyl (e.g., 1-piperazinyl and the like), hexamethyleniminyl (e.g., hexamethylenimin-1-yl and the like), oxazolidinyl (e.g., oxazolidin-3-yl and the like), thiazolidinyl (e.g., thiazolidin-3-yl, thiazolidin-2-yl and the like), imidazolidinyl (e.g., imidazolidin-3-yl and the like), imidazolinyl (e.g., imidazolin-1-yl, imidazolin-2-yl and the like), oxazolinyl (e.g., oxazolin-2-yl and the like), thiazolinyl (e.g., thiazolin-2-yl and the like) and oxazinyl (e.g., oxazin-2-yl and the like); and the like can be mentioned. Of these, azolyl groups (for example, pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl, tetrazolyl and the like), azolinyl groups (for example, imidazolinyl, oxazolinyl, thiazolinyl and the like), azolidinyl groups (for example, pyrrolidinyl, oxazolidinyl, thiazolidinyl, imidazolidinyl and the like) and the like are preferable.

The heterocyclic group represented by $R^1$ optionally has 1 to 3 substituents at substitutable positions. As examples of such substituents, aliphatic hydrocarbon groups, alicyclic hydrocarbon groups, aryl groups, aromatic heterocyclic groups, non-aromatic heterocyclic groups, halogen atoms, nitro groups, optionally substituted amino groups, optionally substituted acyl groups, optionally substituted hydroxy groups, optionally substituted thiol groups, optionally esterified or amidated carboxy groups, oxo groups and the like can be mentioned.

As said aliphatic hydrocarbon groups, straight-chain or branched aliphatic hydrocarbon groups having 1 to 15 carbon atoms, for example, alkyl groups, alkenyl groups, alkynyl groups and the like, can be mentioned.

As preferable examples of the alkyl groups, alkyl groups having 1 to 10 carbon atoms, for example, methyl, ethyl, propyl, isopropyl, butyl, isobutyl, sec.-butyl, t.-butyl, pentyl, isopentyl, neopentyl, t.-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like, can be mentioned.

As preferable examples of the alkenyl groups, alkenyl groups having 2 to 10 carbon atoms, for example, vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like, can be mentioned.

As preferable examples of the alkynyl groups, alkynyl groups having 2 to 10 carbon atoms, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like, can be mentioned.

As said alicyclic hydrocarbon groups, saturated or unsaturated alicyclic hydrocarbon groups having 3 to 12 carbon atoms, for example, cycloalkyl groups, cycloalkenyl groups, cycloalkadienyl groups and the like, can be mentioned.

As preferable examples of the cycloalkyl groups, cycloalkyl groups having 3 to 10 carbon atoms, for example, cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like, can be mentioned.

As preferable examples of the cycloalkenyl groups, cycloalkenyl groups having 3 to 10 carbon atoms, for example, 2-cyclopenten-1-yl, 3-cyclopenten-1-yl, 2-cyclohexen-1-yl, 3-cyclohexen-1-yl and the like, can be mentioned.

As preferable examples of the cycloalkadienyl groups, cycloalkadienyl groups having 4 to 10 carbon atoms, for example, 2,4-cyclopentadien-1-yl, 2,4-cyclohexadien-1-yl, 2,5-cyclohexadien-1-yl and the like, can be mentioned.

As preferable examples of the aryl groups, aryl groups having 6 to 14 carbon atoms, for example, phenyl, naphthyl, anthryl, phenanthryl, acenaphthylenyl and the like, can be mentioned. Of these, phenyl, 1-naphthyl, 2-naphthyl and the like are preferable.

As preferable examples of the aromatic heterocyclic groups, aromatic monocyclic heterocyclic groups, for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like; aromatic condensed heterocyclic groups, for example, benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like; and the like can be mentioned.

As preferable examples of the non-aromatic heterocyclic groups, for example, oxiranyl, azetidinyl, oxetanyl, thietanyl, tetrahydrofuryl, thiolanyl, piperidyl, tetrahydropyranyl, morpholinyl, thiomorpholinyl, piperazinyl, pyrrolidinyl and the like can be mentioned.

As preferable examples of the halogen atoms, fluorine, chlorine, bromine and iodine can be mentioned, with preference given to fluorine and chlorine.

As examples of the optionally substituted amino group, an amino group (—NH$_2$ group) which may be mono- or di-substituted by a substituent selected from alkyl groups having 1 to 10 carbon atoms, which may be substituted by hydroxy, alkenyl groups having 2 to 10 carbon atoms, cycloalkyl groups having 3 to 10 carbon atoms, acyl groups having 1 to 10 carbon atoms (e.g., formyl, $C_{1-9}$ alkyl-carbonyl and the like), aromatic groups having 6 to 12 carbon atoms (e.g., $C_{6-12}$ aryl groups such as phenyl, and the like), aralkyl groups having 7 to 10 carbon atoms (e.g., benzyl and the like) and the like, can be mentioned. As examples of substituted amino groups, methylamino, dimethylamino, ethylamino, diethylamino, dibutylamino, diallylamino, cyclohexylamino, acetylamino, propionylamino, benzoylamino, phenylamino, N-methyl-N-phenylamino, N-methyl-N-benzylamino, N-methyl-N-hydroxyethylamino and the like can be mentioned.

As the acyl group of the optionally substituted acyl group, acyl groups having 1 to 13 carbon atoms, specifically formyl and, for example, groups resulting from the binding of an alkyl group having 1 to 10 carbon atoms, a cycloalkyl group having 3 to 10 carbon atoms, an alkenyl group having 2 to 10 carbon atoms, a cycloalkenyl group having 3 to 10 carbon atoms or an aromatic group having 6 to 12 carbon atoms (e.g., $C_{6-12}$ aryl groups such as phenyl, and the like) and a carbonyl group (e.g., $C_{1-10}$ alkyl-carbonyl groups such as acetyl, propionyl, butyryl, isobutyryl, valeryl, isovaleryl, pivaloyl, hexanoyl, heptanoyl and octanoyl; $C_{3-10}$ cycloalkyl-carbonyl groups such as cyclobutanecarbonyl, cyclopentanecarbonyl, cyclohexanecarbonyl and cycloheptanecarbonyl; $C_{2-10}$ alkenyl-carbonyl groups such as crotonyl; $C_{3-10}$ cycloalkenyl-carbonyl groups such as 2-cyclohexenecarbonyl; $C_{6-12}$ aryl-carbonyl groups such as benzoyl and nicotinoyl; and the like); a phosphono group, and the like can be mentioned. As examples of the substituent of the substituted acyl group, alkyl groups having 1 to 3 carbon atoms, alkoxy groups having 1 to 3 carbon atoms, halogen atoms (e.g., chlorine, fluorine, bromine and the like), nitro, hydroxy, amino and the like can be mentioned.

Referring to the optionally substituted hydroxy group, as examples of the substituted hydroxy group, alkoxy groups which may be substituted by an optionally halogenated $C_{1-6}$ alkyl-carbonylamino (e.g., trifluoroacetylamino and the like); alkenyloxy groups; cycloalkyloxy groups; cycloalkenyloxy groups; aralkyloxy groups; acyloxy groups; aryloxy groups; alkylsulfonyloxy groups; arylsulfonyloxy groups; indanyloxy groups; tetrahydronaphthoxy groups which may be substituted by 1 to 4 $C_{1-6}$ alkyl groups (e.g., methyl and the like); and the like can be mentioned.

As preferable examples of the alkoxy groups, alkoxy groups having 1 to 10 carbon atoms, for example, methoxy, ethoxy, propoxy, isopropoxy, butoxy, isobutoxy, sec.-butoxy, t.-butoxy, pentyloxy, isopentyloxy, neopentyloxy, hexyloxy, heptyloxy, nonyloxy and the like, can be mentioned.

As preferable examples of the alkenyloxy groups, alkenyloxy groups having 2 to 10 carbon atoms, for example, allyloxy, crotyloxy, 2-pentenyloxy, 3-hexenyloxy and the like, can be mentioned.

As preferable examples of the cycloalkyloxy groups, cycloalkyloxy groups having 3 to 7 carbon atoms, for example, cyclobutoxy, cyclopentyloxy, cyclohexyloxy and the like, can be mentioned.

As preferable examples of the cycloalkenyloxy groups, cycloalkenyloxy groups having 5 to 7 carbon atoms, for example, 2-cyclopentenyloxy, 2-cyclohexenyloxy and the like, can be mentioned.

As preferable examples of the aralkyloxy groups, aralkyloxy groups having 7 to 10 carbon atoms, for example, phenyl-$C_{1-4}$ alkyloxy groups (e.g., benzyloxy, phenethyloxy and the like) and the like, can be mentioned.

As preferable examples of the acyloxy groups, acyloxy groups having 2 to 13 carbon atoms, more preferably alkanoyloxy groups having 2 to 4 carbon atoms (e.g., acetyloxy, propionyloxy, butyryloxy, isobutyryloxy and the like) and the like, can be mentioned.

As preferable examples of the aryloxy groups, aryloxy groups having 6 to 14 carbon atoms, for example, phenoxy, naphthyloxy and the like, can be mentioned. Said aryloxy groups (preferably a phenoxy group) optionally have 1 to 3 (preferably 1 or 2) substituents, and as examples of such substituents, halogen atoms (e.g., chlorine, fluorine, bromine and the like); optionally halogenated alkoxy having 1 to 4 carbon atoms (e.g., methoxy, ethoxy, propoxy, isopropoxy, trifluoromethoxy and the like); alkyl groups having 1 to 4 carbon atoms (e.g., methyl, ethyl, propyl, isopropyl, butyl, isobutyl, t.-butyl and the like), which may be substituted by hydroxy, carboxy, $C_{1-6}$ alkoxy-carbonyl (e.g., methoxycarbonyl and the like) or cyano; cyano; carboxy; hydroxy; $C_{6-14}$ aryloxy (e.g., phenoxy and the like); $C_{1-6}$ alkoxy-carbonyl (e.g., methoxycarbonyl and the like); $C_{1-6}$ alkylsulfanyl (e.g., methylsulfanyl and the like); $C_{1-6}$ alkyl-carbonyloxy (e.g., acetyloxy and the like); and the like can be mentioned. As examples of substituted aryloxy groups, 2-,3- or 4-chlorophenoxy; 2-,3- or 4-methoxyphenoxy; 2,3- or 4-methylphenoxy; 2-,3- or 4-cyanophenoxy; 2-,3- or 4-hydroxyphenoxy; and the like can be mentioned.

As preferable examples of the alkylsulfonyloxy groups, alkylsulfonyloxy groups having 1 to 10 carbon atoms, for example, methylsulfonyloxy, ethylsulfonyloxy and the like, can be mentioned.

As preferable examples of the arylsulfonyloxy groups, arylsulfonyloxy groups having 6 to 12 carbon atoms (said arylsulfonyloxy groups may be substituted by a $C_{1-6}$ alkyl group such as methyl), for example, phenylsulfonyloxy, 4-methylphenylsulfonyloxy and the like, can be mentioned.

Referring to the optionally substituted thiol group (optionally substituted mercapto group), as examples of the substituted thiol group, alkylsulfanyl groups which may be substituted by hydroxy; cycloalkylsulfanyl groups; arylsulfanyl groups; heteroarylsulfanyl groups; aralkylsulfanyl groups; heteroarylalkylsulfanyl groups; acylsulfanyl groups; and the like can be mentioned.

As preferable examples of the alkylsulfanyl groups, alkylsulfanyl groups having 1 to 10 carbon atoms (e.g., methylsulfanyl, ethylsulfanyl, propylsulfanyl, isopropylsulfanyl, butylsulfanyl, isobutylsulfanyl, sec.-butylsulfanyl, t.-butylsulfanyl, pentylsulfanyl, isopentylsulfanyl, neopentylsulfanyl, hexylsulfanyl, heptylsulfanyl, nonylsulfanyl and the like) and the like can be mentioned.

As preferable examples of the cycloalkylsulfanyl groups, cycloalkylsulfanyl groups having 3 to 7 carbon atoms (e.g., cyclobutylsulfanyl, cyclopentylsulfanyl, cyclohexylsulfanyl and the like) and the like can be mentioned.

As preferable examples of the arylsulfanyl groups, arylsulfanyl groups having 6 to 14 carbon atoms, which may be substituted by a $C_{1-6}$ alkyl group, for example, phenylsulfanyl, naphthylsulfanyl, 4-methylphenylsulfanyl and the like, can be mentioned.

As examples of the heteroarylsulfanyl groups, thiol groups substituted by the aforementioned aromatic heterocyclic group can be mentioned; of these, 2-pyridylsulfanyl, 3-pyridylsulfanyl, 2-imidazolylsulfanyl, 1,2,4-triazol-5-ylsulfanyl, 2-pyrimidinylsulfanyl and the like are preferable.

As preferable examples of the aralkylsulfanyl groups, aralkylsulfanyl groups having 7 to 10 carbon atoms, for example, phenyl-$C_{1-4}$ alkylsulfanyl groups (e.g., benzylsulfanyl, phenethylsulfanyl and the like) and the like, can be mentioned.

As examples of the heteroarylalkylsulfanyl groups, alkylsulfanyl groups substituted by the aforementioned aromatic heterocyclic groups can be mentioned. Here, the alkylsulfanyl groups can be the same as the above-mentioned alkylsulfanyl groups. As preferable examples of the heteroarylalkylsulfanyl groups, pyridyl-$C_{1-4}$ alkylsulfanyl groups (e.g., 2-pyridylmethylsulfanyl, 3-pyridylmethylsulfanyl and the like) and the like can be mentioned.

As preferable examples of the acylsulfanyl groups, acylsulfanyl groups having 2 to 13 carbon atoms, more preferably alkanoylsulfanyl groups having 2 to 4 carbon atoms (e.g., acetylsulfanyl, propionylsulfanyl, butyrylsulfanyl, isobutyrylsulfanyl and the like) and the like can be mentioned.

Referring to the optionally esterified or amidated carboxy group, as examples of esterified carboxy groups, alkoxycarbonyl groups, aralkyloxycarbonyl groups, aryloxycarbonyl groups, heteroarylalkyloxycarbonyl groups and the like can be mentioned.

As preferable examples of the alkoxycarbonyl groups, alkoxycarbonyl groups having 2 to 5 carbon atoms, for example, $C_{1-4}$ alkoxy-carbonyl groups such as methoxycarbonyl, ethoxycarbonyl, propoxycarbonyl and butoxycarbonyl, and the like, can be mentioned.

As preferable examples of the aralkyloxycarbonyl groups, aralkyloxy-carbonyl groups having 8 to 10 carbon atoms, for example, $C_{7-9}$ aralkyloxy-carbonyl groups such as benzyloxycarbonyl, and the like, can be mentioned.

As preferable examples of the aryloxycarbonyl groups, aryloxycarbonyl groups having 7 to 15 carbon atoms, which may be substituted by a $C_{1-6}$ alkyl group, for example, $C_{6-14}$ aryloxy-carbonyl groups such as phenoxycarbonyl and p-tolyloxycarbonyl, and the like, can be mentioned.

As examples of the heteroarylalkyloxycarbonyl groups, alkyloxycarbonyl groups substituted by the aforementioned aromatic heterocyclic group can be mentioned. Here, the alkyloxycarbonyl groups can be the same as the aforementioned alkoxycarbonyl groups. As preferable examples of the heteroarylalkyloxycarbonyl groups, pyridyl-$C_{1-4}$ alkoxy-carbonyl groups (e.g., 2-pyridylmethoxycarbonyl, 3-pyridylmethoxycarbonyl and the like) and the like can be mentioned.

Referring to the optionally esterified or amidated carboxyl group, as the amidated carboxyl group, the group represented by the formula: —CON($R^2$)($R^3$) wherein $R^2$ and $R^3$ are the same or different and each represents a hydrogen atom, an optionally substituted hydrocarbon group, an optionally substituted hydroxy group or an optionally substituted heterocyclic group, and the like can be mentioned.

Here, as the hydrocarbon group of the "optionally substituted hydrocarbon group" represented by $R^2$ or $R^3$, the aliphatic hydrocarbon groups, alicyclic hydrocarbon groups, aryl groups and the like exemplified as substituents of the heterocyclic group represented by $R^1$, can be mentioned. As the "optionally substituted hydroxy group" represented by $R^2$ or $R^3$, the same as those mentioned above can be mentioned. Also, as the heterocyclic group of the "optionally substituted heterocyclic group" represented by $R^2$ or $R^3$, the aromatic heterocyclic groups and the like exemplified as substituents of the heterocyclic group represented by $R^1$, can be mentioned. As the substituents of the "optionally substituted hydrocarbon group" and "optionally substituted heterocyclic group" represented by $R^2$ or $R^3$, 1 to 3 substituents selected from halogen atoms (e.g., chlorine, fluorine, bromine, iodine and the like), alkyl groups having 1 to 4 carbon atoms, alkoxy groups having 1 to 4 carbon atoms, and the like, can be mentioned.

Provided that the heterocyclic group represented by $R^1$ has an oxo group as a substituent, as examples of the heterocyclic group substituted by an oxo group, azolidinyl groups substituted by one or two oxo groups and the like can be mentioned; as specific examples thereof, for example, 2-oxoimidazolidinyl (e.g., 2-oxoimidazolidin-1-yl and the like), 2,4-dioxoimidazolidinyl (e.g., 2,4-dioxoimidazolidin-3-yl and the like), 2,4-dioxooxazoldinyl (e.g., 2,4-dioxooxazolidin-3-yl and the like), 2,4-dioxothiazolidinyl (e.g., 2,4-dioxothiazolidin-3-yl and the like) and the like can be mentioned.

Referring to the formula (I), the substituents on the heterocyclic group represented by $R^1$, when they are substituents containing an aliphatic hydrocarbon group, an alicyclic hydrocarbon group, an aryl group, an aromatic heterocyclic group, a non-aromatic heterocyclic group and the like, each optionally have 1 or more, preferably 1 to 3, appropriate substituents; as examples of such substituents, alkyl groups having 1 to 6 carbon atoms which may be halogenated, and which may be substituted by a substituent selected from a carboxyl, an alkoxycarbonyl having 2 to 8 carbon atoms, a hydroxy and an optionally halogenated alkoxy having 1 to 4 carbon atoms; alkenyl groups having 2 to 6 carbon atoms; alkynyl groups having 2 to 6 carbon atoms; cycloalkyl groups having 3 to 7 carbon atoms; aryl groups having 6 to 14 carbon atoms (e.g., phenyl, naphthyl and the like); aromatic heterocyclic groups (e.g., thienyl, furyl, pyridyl, oxazolyl, thiazolyl and the like); non-aromatic heterocyclic groups (e.g., tetrahydrofuryl, morpholinyl, thiomorpholinyl, piperidyl, pyrrolidinyl, piperazinyl and the like); aralkyl groups having 7 to 9 carbon atoms (e.g., benzyl and the like); amino groups; N-mono($C_{1-4}$)alkylamino groups; N, N-di($C_{1-4}$)alkylamino groups; acylamino groups having 2 to 8 carbon atoms (e.g., $C_{1-7}$ alkyl-carbonylamino such as acetylamino and propionylamino; benzoylamino and the like); amidino groups; acyl groups having 2 to 8 carbon atoms (e.g., $C_{1-7}$ alkyl-carbonyl such as acetyl and the like); carbamoyl groups; N-mono($C_{1-4}$)alkylcarbamoyl groups; N, N-di($C_{1-4}$)alkylcarbamoyl groups; sulfamoyl groups; N-mono($C_{1-4}$)alkylsulfamoyl groups; N, N-di($C_{1-4}$)alkylsulfamoyl groups; carboxyl groups; alkoxycarbonyl groups having 2 to 8 carbon atoms; hydroxy groups; optionally halogenated alkoxy groups having 1 to 4 carbon atoms; alkenyloxy groups having 2 to 5 carbon atoms; cycloalkyloxy groups having 3 to 7 carbon atoms; aralkyloxy groups having 7 to 9 carbon atoms (e.g., benzyloxy and the like); aryloxy groups having 6 to 14 carbon atoms (e.g., phenyloxy, naphthyloxy and the like); mercapto groups; optionally halogenated alkylsulfanyl groups having 1 to 4 carbon atoms; aralkylsulfanyl groups having 7 to 9 carbon atoms (e.g., benzylsulfanyl and the like); arylsulfanyl groups having 6 to 14 carbon atoms (e.g., phenylsulfanyl, naphthylsulfanyl and the like); sulfo groups; cyano groups; azide groups; nitro groups; nitroso groups; halogen atoms (e.g., fluorine, chlorine, bromine, iodine); and the like can be mentioned.

Referring to the formula (I), as the "optionally substituted hydroxy group", "optionally substituted thiol group" and "optionally substituted amino group" represented by $R^1$, those exemplified as substituents of the heterocyclic group represented by $R^1$ can be mentioned.

Referring to the formula (I), $R^1$ is preferably an optionally substituted heterocyclic group. As $R^1$, an optionally substituted nitrogen-containing heterocyclic group is preferable, and an optionally substituted 5-membered nitrogen-containing aromatic heterocyclic group is more preferable. Particularly preferred is an optionally substituted imidazolyl group. As preferable examples of $R^1$, imidazolyl groups which may be substituted by a $C_{1-10}$ alkyl group, and the like can be mentioned.

Referring to the formula (I), as the "optionally substituted acyl group", "optionally substituted hydroxy group" and "optionally esterified or amidated carboxy group" represented by A, those exemplified as substituents of the heterocyclic group represented by $R^1$, and the like can be mentioned.

Also, as the "optionally substituted heterocyclic group" represented by A, those exemplified as $R^1$ can be mentioned.

Referring to the formula (I), A is preferably an optionally substituted hydroxy group. A is more preferably an optionally substituted aryloxy group; as specific examples thereof, aryloxy groups having 6 to 14 carbon atoms (e.g., phenoxy and the like), which optionally have 1 to 3 substituents selected from halogen atoms (e.g., chlorine, fluorine, bromine and the like); optionally halogenated alkoxy having 1 to 4 carbon atoms (e.g., methoxy, ethoxy, propoxy, isopropoxy, trifluoromethoxy and the like); alkyl having 1 to 4 carbon atoms (e.g., methyl, ethyl, propyl, isopropyl, butyl, isobutyl, t.-butyl, and the like), which may be substituted by hydroxy, carboxy, a $C_{1-6}$ alkoxy-carbonyl (e.g., methoxycarbonyl and the like) or cyano; cyano; carboxy; hydroxy; $C_{6-14}$ aryloxy (e.g., phenoxy and the like); $C_{1-6}$ alkoxy-carbonyl (e.g., methoxycarbonyl and the like); $C_{1-6}$ alkylsulfanyl (e.g., methylsulfanyl and the like); and $C_{1-6}$ alkyl-carbonyloxy (e.g., acetyloxy and the like); can be mentioned.

Of these, aryloxy groups having 6 to 14 carbon atoms (preferably a phenoxy group) substituted by an alkyl group having 1 to 4 carbon atoms are preferable.

Referring to the formula (I), as examples of the aromatic group of the "optionally substituted aromatic group" represented by B, aromatic hydrocarbon groups, aromatic heterocyclic groups and the like can be mentioned.

As preferable examples of the aromatic hydrocarbon groups, $C_{6-14}$ aryl groups (e.g., phenyl, naphthyl) and the like can be mentioned.

As preferable examples of the aromatic heterocyclic groups, those exemplified as substituents of the heterocyclic group represented by $R^1$ can be mentioned; of these, furyl, thienyl, pyridyl, quinolyl and the like are preferable.

As examples of the substituents of the "optionally substituted aromatic group" represented by B, 1 to 3 substituents selected from halogen atoms, nitro groups, cyano groups, optionally substituted alkoxy groups, optionally substituted alkyl groups, optionally substituted cycloalkyl groups and the like, can be mentioned.

Here, as examples of the halogen atoms, fluorine, chlorine, bromine, iodine and the like can be mentioned.

As the alkoxy group of the optionally substituted alkoxy group, those exemplified as substituents of the heterocyclic group represented by $R^1$ can be mentioned; of these, straight-chain or branched alkoxy groups having 1 to 6 carbon atoms are preferable.

As the alkyl group of the optionally substituted alkyl group, those exemplified as substituents of the heterocyclic group represented by $R^1$ can be mentioned; of these, straight-chain or branched alkyl groups having 1 to 6 carbon atoms are preferable.

As the cycloalkyl group of the optionally substituted cycloalkyl group, those exemplified as substituents of the heterocyclic group represented by $R^1$ can be mentioned; of these, cycloalkyl groups having 3 to 7 carbon atoms are preferable.

As examples of substituents of the aforementioned "optionally substituted alkoxy group", "optionally substituted alkyl group" and "optionally substituted cycloalkyl group", 1 to 3 substituents selected from halogen atoms (e.g., fluorine, chlorine, bromine, iodine), hydroxy groups, alkoxy groups having 1 to 6 carbon atoms, and the like, can be mentioned.

As examples of substituted alkoxy groups, trifluoromethoxy, difluoromethoxy, 2,2,2-trifluoroethoxy, 1,1-difluoroethoxy and the like can be mentioned.

As examples of substituted alkyl groups, trifluoromethyl, difluoromethyl, 2,2,2-trifluoroethyl, trichloromethyl, 1-hydroxymethyl, methoxymethyl, ethoxymethyl, 2-methoxyethyl, 2,2-dimethoxyethyl and the like can be mentioned.

Referring to the formula (I), B is preferably an optionally substituted aromatic hydrocarbon group, more preferably an optionally substituted phenyl group. Particularly preferred is a phenyl group which may be substituted by a halogen atom.

Referring to the formula (I), X represents an oxygen atom, a sulfur atom or an optionally substituted nitrogen atom (preferably an oxygen atom or a sulfur atom).

As examples of the "optionally substituted nitrogen atom" represented by X, —$NR^4$— wherein $R^4$ represents a hydrogen atom, an optionally substituted hydrocarbon group, an optionally substituted acyl group or an optionally substituted heterocyclic group and the like can be mentioned.

Here, as the "optionally substituted hydrocarbon group" represented by $R^4$, those exemplified as $R^2$ can be mentioned.

As the "optionally substituted acyl group" represented by $R^4$, those exemplified as substituents of the heterocyclic group represented by $R^1$ can be mentioned.

As the "optionally substituted heterocyclic group" represented by $R^4$, the same as the "optionally substituted heterocyclic group" represented by $R^1$ can be mentioned.

$R^4$ is preferably a hydrogen atom, an optionally substituted hydrocarbon group and the like, more preferably a hydrogen atom, an optionally substituted alkyl group and the like, with preference given to a hydrogen atom, a lower ($C_{1-4}$) alkyl group and the like.

X is preferably an oxygen atom.

Referring to the formula (I), as the divalent hydrocarbon group represented by Y, a divalent aliphatic hydrocarbon group, a divalent alicyclic hydrocarbon group, a divalent aromatic hydrocarbon group and the like can be mentioned.

The divalent aliphatic hydrocarbon group represented by Y may be straight-chain or branched, and may be saturated or unsaturated. As said aliphatic hydrocarbon group, those divalent groups formed by removing one hydrogen atom from the aliphatic hydrocarbon group exemplified as substituents of the heterocyclic group represented by $R^1$, and the like, can be mentioned; of these, those having 1 to 7 carbon atoms are preferred; as specific examples thereof, saturated ones (e.g., alkylene groups), for example, —$CH_2$—, —$CH(CH_3)$—, —$(CH_2)_2$—, —$CH(C_2H_5)$—, —$(CH_2)_3$—, —$(CH_2)_4$—, —$(CH_2)_5$—, —$(CH_2)_6$—, —$(CH_2)_7$— and the like; and unsaturated ones (e.g., alkenylene groups, alkadienylene groups, alkatrienylene groups), for example, —CH=CH—, —C(CH_3)=CH—, —CH=CH—$CH_2$—, —C($C_2H_5$)=CH—, —$CH_2$—CH=CH—$CH_2$—, —$CH_2$—$CH_2$—CH=CH—$CH_2$—, —CH=CH—CH=CH—$CH_2$—, —CH=CH—CH=CH—CH=CH—$CH_2$— and the like; can be mentioned.

As the divalent alicyclic hydrocarbon group represented by Y, those divalent groups formed by removing one hydrogen atom from the alicyclic hydrocarbon group exemplified as substituents of the heterocyclic group represented by $R^1$, and the like, can be mentioned.

As the divalent aromatic hydrocarbon group represented by Y, those divalent groups formed by removing one hydrogen atom from the aryl group exemplified as substituents of the heterocyclic group represented by $R^1$, and the like, can be mentioned.

Referring to the formula (I), as the divalent heterocyclic group represented by Y, divalent aromatic heterocyclic groups, divalent non-aromatic hydrocarbon groups and the like can be mentioned.

As the divalent aromatic heterocyclic group represented by Y, those divalent groups formed by removing one hydrogen atom from the aromatic heterocyclic group exemplified as substituents of the heterocyclic group represented by $R^1$, and the like, can be mentioned.

As the divalent non-aromatic heterocyclic group represented by Y, those divalent group formed by removing one hydrogen atom from the non-aromatic heterocyclic group exemplified as substituents of the heterocyclic group represented by $R^1$, and the like, can be mentioned.

Referring to the formula (I), Y is preferably a divalent aliphatic hydrocarbon group, more preferably a divalent aliphatic hydrocarbon group having 1 to 4 carbon atoms, particularly preferably an alkylene group having 1 to 4 carbon atoms. As preferable specific examples of Y, for example, —$(CH_2)_3$— and —$(CH_2)_4$— can be mentioned.

As Compound (I), the following compounds are preferable.

Compounds of the formula (I), wherein A is an aryloxy group substituted by an alkyl group, preferably an aryloxy group having 6 to 14 carbon atoms (preferably phenoxy) substituted by an alkyl group having 1 to 4 carbon atoms, more preferably a group represented by the formula:

wherein $C_{1-4}$ alkyl represents methyl, ethyl, propyl, isopropyl or the like, preferably methyl or the like; $R^1$ is an optionally substituted 5-membered nitrogen-containing aromatic heterocyclic group, preferably an optionally substituted imidazolyl group, more preferably an imidazolyl group which may be substituted by a $C_{1-10}$ alkyl group, particularly preferably a group represented by the formula:

wherein $C_{1-10}$ alkyl group represents methyl, ethyl, propyl, isopropyl, butyl, pentyl, hexyl or the like, preferably a $C_{1-4}$ alkyl such as methyl, ethyl, propyl or isopropyl, more preferably methyl or the like;

B is an optionally substituted phenyl group, preferably a phenyl group which may be substituted by a halogen atom, more preferably a group represented by the formula:

wherein Hal represents a halogen atom such as fluorine, chlorine, bromine or iodine, preferably chlorine;

X is an oxygen atom; and

Y is a divalent aliphatic hydrocarbon group, preferably a divalent aliphatic hydrocarbon group having 1 to 4 carbon atoms, more preferably a $C_{1-4}$ alkylene such as —$CH_2$—, —$(CH_2)_2$—, —$(CH_2)_3$— or —$(CH_2)_4$—, particularly preferably —$(CH_2)_3$—.

As preferable specific examples of the compound represented by the formula (I), for example, Compounds (1) to (7) shown below and the like can be mentioned.

(1) 4-(4-chlorophenyl)-5-[3-(2-methoxyphenoxy)propyl]-2-(2-methyl-1-imidazolyl)oxazole (2) 3-[3-[4-(4-chlorophenyl)-2-(2-methyl-1-imidazolyl)-5-oxazolyl]propyl]-1-methyl-2,4-imidazolidinedione (3) 4-(4-chlorophenyl)-5-[3-(3-methoxyphenoxy)propyl]-2-(2-methyl-1-imidazolyl)oxazole (4) 4-(4-chlorophenyl)-5-[3-(4-methoxyphenoxy)propyl]-2-(2-methyl-1-imidazolyl)oxazole (5) 4-(4-chlorophenyl)-2-(2-methyl-1-imidazolyl)-5-[3-(2-methylphenoxy)propyl]oxazole
(6) 4-(4-chlorophenyl)-2-(2-methyl-1-imidazolyl)-5-[3-(3-methylphenoxy)propyl]oxazole
(7) 5-[3-(4-chloro-2-methylphenoxy)propyl]4-(4-chlorophenyl)-2-(2-methyl-1-imidazolyl)oxazole These compounds are hereinafter sometimes simply abbreviated as Compound (1), Compound (2) and the like.

The salt of Compound (I) is preferably a pharmaceutically acceptable salt; as examples of such salts, a salt with an inorganic base, a salt with an organic base, a salt with an inorganic acid, a salt with an organic acid, a salt with a basic or acidic amino acid and the like can be mentioned.

As preferable examples of the salt with an inorganic base, alkali metal salts such as sodium salt and potassium salt; alkaline earth metal salts such as calcium salt and magnesium salt; and aluminum salt, ammonium salt and the like can be mentioned.

As preferable examples of the salt with an organic base, salts with, for example, trimethylamine, triethylamine, pyridine, picoline, ethanolamine, diethanolamine, triethanolamine, dicyclohexylamine, N, N'-dibenzylethylenediamine and the like, can be mentioned.

As preferable examples of the salt with an inorganic acid, salts with, for example, hydrochloric acid, hydrobromic acid, nitric acid, sulfuric acid, phosphoric acid and the like, can be mentioned.

As preferable examples of the salt with an organic acid, salts with, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like, can be mentioned.

As preferable examples of the salt with a basic amino acid, salts with, for example, arginine, lysine, ornithine and the like, can be mentioned.

As preferable examples of the salt with an acidic amino acid, salts with, for example, aspartic acid, glutamic acid and the like, can be mentioned.

Compound (I) or a salt thereof can be produced by a method known per se. As examples of such methods, methods described in WO 01/14372, JP-A-58-183676 (EP-A 92239), JP-A-59-190979, JP-A-9-323983 (WO 97/36882) and the like or methods based thereon can be mentioned.

Compound (I) of the present invention may be used as a prodrug; here a prodrug of Compound (I) refers to a compound capable of being converted to Compound (I) or a salt thereof by an action of an enzyme, gastric juice or the like under physiological conditions in vivo, that is, a compound capable of being converted to Compound (I) upon enzymatic oxidation, reduction, hydrolysis or the like, or a compound capable of being converted to Compound (I) upon hydrolysis or the like by gastric juice or the like. As the prodrug of Compound (I), compounds derived by acylation, alkylation or phosphorylation of the amino group of Compound (I) (for example, compounds derived by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group of Compound (I) and the like); compounds derived by acylation, alkylation, phosphorylation or boration of the hydroxyl group of Compound (I) (for example, compounds derived by acetylation, palmitoylation, propanoylation, pivaloylation, succinylation, fumarylation, alanylation or dimethylaminomethylcarbonylation of the hydroxyl group of Compound (I) and the like); and compounds derived by esterification or amidation of the carboxyl group of Compound (I) (for example, compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation of the carboxyl group of Compound (I) and the like). These compounds can be produced from Compound (I) by a method known per se.

The prodrug of Compound (I) may be one capable of being converted to Compound (I) under physiological conditions, as described on pages 163 to 198 in "*Iyakuhin No Kaihatsu (Development of Drugs)*", vol. 7, Bunshi Sekkei (Molecular Designing), published by Hirokawa Shoten, 1990.

Compound (I) may be a hydrate and may be labeled with an isotope (e.g., $^3$H, $^{14}$C, $^{35}$S, $^{125}$I and the like) and the like.

Compound (I), a salt-thereof or a prodrug thereof (hereinafter sometimes abbreviated as the compound of the present invention) is low in toxicity and can be administered safely to mammals (e.g., humans, mice, rats, rabbits, dogs, cats, bovines, horses, swines, monkeys and the like).

Although the VDAC regulator, apoptosis inhibitor or mitochondria function ameliorator of the present invention (these are hereinafter sometimes abbreviated as the agent of the present invention) may be the compound of the present invention itself, they are generally obtained by formulating a preparation according to a method known per se, using the compound of the present invention and a pharmacologically acceptable carrier.

As examples of the VDAC in the VDAC regulator, VDAC-1, VDAC-2, VDAC-3 and the like can be mentioned. Also, the VDAC regulator is capable of regulating (normalizing by promotion or inhibition) a VDAC function (e.g., transportation of solutes involved in energy production in mitochondria, glycolipid metabolism, apoptosis, intracellular Ca homeostasis and the like; and interaction with factors such as hexokinase and Bax). The VDAC regulator is preferably a VDAC inhibitor.

Referring to the mitochondria function ameliorator, as examples of the mitochondria function, substrate channel functions (e.g., VDAC), glycolipid metabolism, energy production, apoptosis regulation, Ca-buffering function and the like can be mentioned. The mitochondria function ameliorator of the present invention is capable of stabilizing (normalizing or suppressing abnormal changes in) the membrane potential and respiratory activity of mitochondria by ameliorating the aforementioned mitochondria functions.

As the pharmacologically acceptable carrier, employed are various organic or inorganic carrier substances conventionally used as pharmaceutical materials; as specific examples thereof, excipients, lubricants, binders and disintegrants in solid preparations; solvents, solubilizers, suspending agents, isotonizing agents, buffers and soothing agents in liquid preparations, and the like can be mentioned. In formulating a preparation, pharmaceutical additives such as antiseptics, antioxidants, coloring agents and sweeteners may be used as necessary.

As preferable examples of the excipients, lactose, saccharose, D-mannitol, D-sorbitol, starch, pre-gelatinized starch, dextrin, crystalline cellulose, low-substituted hydroxypropylcellulose, carboxymethylcellulose sodium, acacia, pullulan, light silicic anhydride, synthetic aluminum silicate, magnesium aluminometasilicate, xylitol, sorbitol, erythritol and the like can be mentioned.

As preferable examples of the lubricants, magnesium stearate, calcium stearate, talc, colloidal silica, polyethylene glycol 6000 and the like can be mentioned.

As preferable examples of the binders, pre-gelatinized starch, sucrose, gelatin, acacia, methylcellulose, carboxymethylcellulose, carboxymethylcellulose sodium, crystalline cellulose, saccharose, D-mannitol, trehalose, dextrin, pullulan, hydroxypropylcellulose, hydroxypropylmethylcellulose, polyvinylpyrrolidone and the like can be mentioned.

As preferable examples of the disintegrants, lactose, saccharose, starch, carboxymethylcellulose, carboxymethylcellulose calcium, croscarmellose sodium, carboxymethylstarch sodium, low-substituted hydroxypropylcellulose, light silicic anhydride, calcium carbonate and the like can be mentioned.

As preferable examples of the solvents, water for injection, physiological saline, Ringer's solution, alcohol, propylene glycol, polyethylene glycol, sesame oil, corn oil, olive oil, cotton seed oil and the like can be mentioned.

As preferable examples of the solubilizers, polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like can be mentioned.

As preferable examples of the suspending agents, surfactants, for example, stearyl triethanolamine, sodium lauryl sulfate, laurylaminopropionic acid, lecithin, benzalkonium chloride, benzethonium chloride and glycerol monostearate; hydrophilic polymers, for example, polyvinyl alcohol, polyvinylpyrrolidone, carboxymethylcellulose sodium, methylcellulose, hydroxymethylcellulose, hydroxyethylcellulose and hydroxypropylcellulose; polysorbates, polyoxyethylene hydrogenated castor oil and the like can be mentioned.

As preferable examples of the isotonizing agents, sodium chloride, glycerol, D-mannitol, D-sorbitol, glucose, xylitol, fructose and the like can be mentioned.

As preferable examples of the buffers, buffer solutions of phosphates, acetates, carbonates, citrates and the like can be mentioned.

As preferable examples of the soothing agents, propylene glycol, lidocaine hydrochloride, benzyl alcohol and the like can be mentioned.

As preferable examples of the antiseptics, para-hydroxybenzoate esters, chlorobutanol, benzyl-alcohol, phenethyl alcohol, dehydroacetic acid, sorbic acid and the like can be mentioned.

As preferable examples of the antioxidants, sulfites, ascorbates and the like can be mentioned.

As preferable examples of the coloring agents, water-soluble colored tar dyes (e.g., food colors such as Food Color Red No. 2 and No. 3, Food Color Yellow No. 4 and No. 5 and Food Color Blue No. 1 and No. 2), water-insoluble lake colors (e.g., aluminum salts of the aforementioned water-soluble edible tar colors), natural colors (e.g., β-carotene, chlorophyll, red iron oxide and the like) and the like can be mentioned.

As preferable examples of the sweeteners, saccharin sodium, dipotassium glycyrrhizinate, aspartame, stevia and the like can be mentioned.

As examples of the dosage form of the agent of the present invention, oral preparations such as tablets (including sublingual tablets and intraorally disintegrating tablets), capsules (including soft capsules and microcapsules), granules, powders, troches, syrups, emulsions and suspensions; and parenteral preparations such as injections (e.g., subcutaneous injections, intravenous injections, intramuscular injections, intraperitoneal injections, drip infusions and the like), external preparations (e.g., transdermal preparations, ointments and the like), suppositories (e.g., rectal suppositories, vaginal suppositories and the like), pellets, transnasal preparations, transpulmonary preparations (inhalants) and eye drops; can be mentioned. These preparations may be controlled-release preparations (e.g., sustained-release microcapsules and the like) such as rapid-release preparations or sustained-release preparations.

These preparations can be produced according to methods conventionally used in the field of pharmaceutical manufacturing technology, for example, methods described in the Japanese Pharmacopoeia, and the like. The content of the compound of the present invention in the agent of the present invention ranges is, for example, 0.1 to 100% by weight.

Methods of producing the oral preparations and parenteral preparations are specifically described below.

The oral preparations are produced by adding, to the active ingredient, for example, an excipient (e.g., lactose, saccharose, starch, D-mannitol, xylitol, sorbitol, erythritol, crystalline cellulose, light silicic anhydride and the like), a disintegrant (e.g., calcium carbonate, starch, carboxymethylcellulose, carboxymethylcellulose calcium, low-substituted hydroxypropylcellulose, croscarmellose sodium, carboxymethyl starch sodium, light silicic anhydride and the like), a binder (e.g., pre-gelatinized starch, acacia, carboxymethylcellulose, hydroxypropylcellulose, hydroxypropylmethylcellulose, polyvinylpyrrolidone, crystalline cellulose, methylcellulose, saccharose, D-mannitol, trehalose, dextrin and the like), a lubricant (e.g., talc, magnesium stearate, calcium stearate, colloidal silica, polyethylene glycol 6000 and the like) and the like, and carrying out compression molding.

Furthermore, for the purpose of masking the taste or imparting an enteric or sustained-release property, the oral preparations may be coated by a method known per se. As examples of the coating agent, enteric polymers (e.g., cellulose acetate phthalate, methacrylic acid copolymer L, methacrylic acid copolymer LD, methacrylic acid copolymer S, hydroxypropylmethylcellulose phthalate, hydroxypropylmethylcellulose acetate succinate, carboxymethylethylcellulose and the like), gastric-soluble polymers (e.g., polyvinyl acetal diethylaminoacetate, aminoalkylmethacrylate copolymer E and the like), water-soluble polymers (e.g., hydroxypropylcellulose, hydroxypropylmethylcellulose and the like), water-insoluble polymers (e.g., ethylcellulose, aminoalkylmethacrylate copolymer RS, ethyl acrylate/methyl methacrylate copolymer and the like), wax and the like are used. When coating is carried out, plasticizers such as polyethylene glycol, light-shielding agents such as titanium oxide and iron sesquioxide may be used along with the above-mentioned coating agent.

Injections are produced by dissolving, suspending or emulsifying the active ingredient in an aqueous solvent (e.g., distilled water, physiological saline, Ringer's solution and the like) or an oily solvent (e.g., vegetable oils such as olive oil, sesame oil, cotton seed oil and corn oil; propylene glycol, macrogol, tricaprylin and the like) or the like, along with a dispersant (e.g., Tween 80 (manufactured by Atlas Powder Company, USA), HCO 60 (manufactured by Nikko Chemicals), polyethylene glycol, carboxymethylcellulose, sodium alginate and the like), a preservative (e.g., methylparaben, propylparaben, benzyl alcohol, chlorobutanol, phenol and the like), an isotonizing agent (e.g., sodium chloride, glycerol, D-sorbitol, D-mannitol, xylitol, glucose, fructose and the like) and the like.

Where desired, additives such as solubilizers (e.g., sodium salicylate, sodium acetate, polyethylene glycol, propylene glycol, D-mannitol, trehalose, benzyl benzoate, ethanol, trisaminomethane, cholesterol, triethanolamine, sodium carbonate, sodium citrate and the like), suspending agents (e.g., surfactants such as stearyl triethanolamine, sodium lauryl sulfate, laurylaminopropionic acid, lecithin, benzalkonium chloride, benzethonium chloride and glyceryl monostearate; hydrophilic polymers such as polyvinyl alcohol, polyvinylpyrrolidone, carboxymethylcellulose sodium, methylcellulose, hydroxymethylcellulose, hydroxyethylcellulose and hydroxypropylcellulose, and the like), buffering agents (e.g., buffer solutions of phosphates, acetates, carbonates, citrates and the like, and the like), stabilizers (e.g., human serum albumin and the like), soothing agents (e.g., propylene glycol, lidocaine hydrochloride, benzyl alcohol and the like), antiseptics (e.g., p-hydroxybenzoic acid esters, chlorobutanol, benzalkonium chloride, benzyl alcohol, phenethyl alcohol, dehydroacetic acid, sorbic acid and the like) and the like may be used.

The external preparations are produced by making the active ingredient into a solid, semi-solid or liquid composition. For example, the above-mentioned solid composition is produced by using the active ingredient as is, or by adding an excipient (e.g., lactose, D-mannitol, starch, crystalline cellulose, saccharose and the like), a thickener (e.g., natural gums, cellulose derivatives, acrylic acid polymers and the like) and the like, and mixing and powdering them. The above-mentioned liquid composition is produced in almost the same manner as the case of the injections. The semi-solid composition is preferably an aqueous or oily gel or an ointment. Also, each of these compositions may contain a pH regulator (e.g., phosphoric acid, citric acid, hydrochloric acid, sodium hydroxide and the like), an antiseptic (e.g., p-hydroxybenzoic acid esters, chlorobutanol, benzalkonium chloride, benzyl alcohol, phenethyl alcohol, dehydroacetic acid, sorbic acid and the like) and the like.

The suppositories are produced by making the active ingredient into an oily or aqueous solid, semi-solid or liquid composition. As examples of the oily base used for the production of said composition, higher fatty acid glycerides [e.g., cacao butter, Witepsols (manufactured by Huels Aktiengesellschaft, Germany) and the like], intermediate fatty acid triglycerides [e.g., miglyols (manufactured by Huels Aktiengesellschaft, Germany) and the like], vegetable oils (e.g., sesame oil, soy bean oil, cotton seed oil and the like) and the like can be mentioned. As examples of the aqueous base, polyethylene glycols, propylene glycol and the like can be mentioned. Also, as examples of the aqueous gel base, natural gums, cellulose derivatives, vinyl polymers, acrylic acid polymers and the like can be mentioned.

The agent of the present invention can be used as an agent for the prophylaxis or treatment of diseases, for example, Down's syndrome, nervous system diseases, viral diseases (e.g., AIDS, fulminant hepatitis and the like), myelodysplastic diseases (e.g., aplastic anemia and the like), liver diseases (e.g., alcoholic hepatitis, hepatitis B, hepatitis C and the like), joint diseases (e.g., osteoarthritis and the like), ear diseases (e.g., deafness, tinnitus) and the like.

The aforementioned nervous system diseases mean abnormalities, disorders or damages of the brain, spinal cord, autonomic ganglia, central nerves, peripheral nerves, cranial nerves, spinal nerves, nerve plexus and the like; as specific examples thereof, amyotrophic lateral sclerosis, retinitis pigmentosa, cerebellar degeneration, diabetic neuropathy, multiple sclerosis, Alzheimer-type senile dementia, Parkinson's disease, Huntington's chorea, schizophrenia and the like can be mentioned. Also, as specific examples of the nervous system diseases, neuropathies due to cancer treatment, and the like, can also be mentioned.

Also, the agent of the present invention can also be used as an agent for the prophylaxis or treatment of diseases such as diabetic cardiomyopathy; cerebral ischemic diseases (e.g., cerebral infarction, cerebral stroke and the like); depression; inflammatory bowel diseases (e.g., inflammatory colitis); chronic pains (e.g., cancerous pain and the like); problematic behavior associated with dementia (e.g., wandering, aggressive behavior and the like); anxiety; epilepsy; numbness or pain due to wounds; diabetes (e.g., type 1 diabetes, type 2 diabetes, gestational diabetes and the like); impaired glucose tolerance (IGT); hyperlipidemia (e.g., hypertriglyceridemia, hypercholesterolemia, hypo-HDL-emia, postprandial hyperlipidemia and the like); hyperinsulinemia; obesity; hyperphagia; hypertension; cardiovascular diseases (e.g., myocardial infarction, atherosclerosis and the like); neurogenic pains (e.g., painful neuropathy, postherpetic neuralgia, back pain, trigeminal neuralgia, carpal tunnel syndrome, phantom pain); autonomic nerve abnormalities (e.g., diabetic autonomic neuropathy, asymptomatic hypoglycemia, gastroparesis, neurogenic diarrhea and constipation, erectile dysfunction, orthostatic hypotension, arrhythmia, heart failure, painless myocardial infarction, dyshidrosis, neurogenic bladder); bladder dysfunctions (e.g., bladder reflex disorder); impaired hearing; diabetic foot lesions; bone diseases (e.g., osteoporosis); joint diseases (e.g., Charcot's joint, osteoarthritis, rheumatism); Hirschsprung's disease; and the like, or syndromes complicated with some of these diseases (e.g., syndrome X, visceral obesity syndrome and the like).

Furthermore, the agent of the present invention can also be used for the secondary prophylaxis and the suppression of development of the above-mentioned various diseases.

Furthermore, the agent of the present invention is also useful as a nerve protector; a nerve function ameliorator; a drug for ameliorating peripheral neuropathy or cerebral metabolic disorder; a drug for promoting the cure of skin injury caused by metabolic or endocrine system diseases such as diabetes, and by wound; a pancreas regenerator (drug for restoring pancreatic function); a kidney regenerator (drug for restoring renal function); a drug for ameliorating or suppressing pains (e.g., neurogenic pain); a prophylactic drug for inferior limb amputation; a prophylactic drug for sudden death; and the like.

Furthermore, the mitochondria function ameliorator of the present invention is also useful as an agent for the prophylaxis or treatment of various diseases or symptoms associated with mitochondria functional abnormalities (e.g., convulsion, myoclonus, ataxia, cerebral stroke, intellectual deterioration, migraine, psychiatric symptoms, dystonia, myelopathy, psychomotor developmental retardation, muscular weakness, easy fatigability, hypercreatinekinasemia, conduction disturbance, Wolff-Parkinson-White syndrome, cardiomyopathy, optic nerve atrophy, external ophthalmoplegia, pigmentary degeneration of retina, liver dysfunction, Fanconi syndrome, Bartter syndrome, glornerular lesions, myoglobinuria, diabetes, exocrine insufficiency, sideroblastic anemia, pancytopenia, sensorineural deafness, diarrhea, constipation, hypohydrosis, hypertrichosis, short stature, hypocalcemia, infertility) and the like.

Although the dose of the agent of the present invention varies depending on administration subject, route of administration, symptoms and the like, when the agent of the present invention is orally administered to an adult, its dose as the amount of the compound of the present invention, which is the active ingredient, per dose, is generally about 0.05 to 500 mg/kg body weight, preferably about 0.5 to 100 mg/kg body weight. It is desirable that this dose be administered once to three times a day.

For example, when the agent of the present invention is orally administered to an adult patient with Down's syndrome, its dose as the amount of the compound of the present invention, which is the active ingredient, per dose, is generally about 0.05 to 50 mg/kg body weight, preferably about 0.2 to 4 mg/kg body weight. It is desirable that this dose be administered once to three times a day.

The agent of the present invention can be used in combination with a drug (hereinafter sometimes abbreviated as concomitant drug) such as a therapeutic agent for diabetes, a therapeutic agent for diabetic complications, a therapeutic agent for hyperlipidemia, a hypotensive agent, an antiobesity agent, a diuretic, a chemotherapeutic agent, an immunotherapeutic agent, a cachexia ameliorator, an agent acting on peripheral and central nerves, a therapeutic agent for ulcers and an anti-inflammatory agent. The concomitant drug may be a low-molecular compound, and may also be a high-molecular protein, polypeptide or antibody, or a vaccine and the like.

On such occasions, the times of administration of the agent of the present invention and the concomitant drug are not limited; these may be administered to the administration subject simultaneously or at time intervals.

The dosage form of the concomitant drug is not particularly limited, as long as the agent of the present invention and the concomitant drug are combined at the time of administration. As examples of such dosage forms, 1) administration of a single preparation obtained by simultaneously formulating the agent of the present invention and the concomitant drug into a preparation, 2) simultaneous administration of two kinds of preparations obtained by separately formulating the agent of the present invention and the concomitant drug into different preparations via the same route of administration, 3) administration of two kinds of preparations obtained by separately formulating the agent of the present invention and the concomitant drug into different preparations via the same route of administration at a time interval, 4) simultaneous administration of two kinds of preparations obtained by separately formulating the agent of the present invention and the concomitant drug into different preparations via different routes of administration, 5) administration of two kinds of preparations obtained by. separately formulating the agent of the present invention and the concomitant drug into different preparations via different routes of administration at a time interval (for example, administration of the agent of the present invention and the concomitant drug in this order, or administration in the reverse order) and the like can be mentioned.

The dose of the concomitant drug can be appropriately selected based on the clinically employed dose.

Also, the mixing ratio of the agent of the present invention and the concomitant drug can be appropriately selected according to administration subject, route of administration, target disease, symptoms, combination and the like. For example, when the administration subject is a human, the concomitant drug may be used at 0.01 to 100 parts by weight per part by weight of the agent of the present invention.

As the therapeutic agent for diabetes, insulin preparations (e.g., animal insulin preparations extracted from the bovine or swine pancreas; human insulin preparations synthesized by gene engineering using *Escherichia coli* or yeast; insulin-zinc; protamine-insulin-zinc; fragments or derivatives of insulin (e.g., INS-1 and the like) and the like), insulin sensitizers (e.g., pioglitazone hydrochloride, troglitazone, rosiglitazone or its maleate, Reglixane (JTT-501), Netoglitazone (MCC-555), YM-440, GI-262570, KRP-297, FK-614, CS-011, compounds described in WO99/58510 (for example, (E)-4-[4-(5-methyl-2-phenyl-4-oxazolylmethoxy)benzyloxyimino]-4-phenylbutyric acid), Tesaglitazar (AZ-242), Ragaglitazar (NN-622), BMS-298585, ONO-5816, BM-13-1258, LM-4156, MBX-102, LY-519818, MX-6054, LY-510929 and the like), α-glucosidase inhibitors (e.g., voglibose, acarbose, miglitol, emiglitate and the like), biguanide agents (e.g., phenformin, metformin, buformin and the like), sulfonylurea agents (e.g., tolbutamide, glibenclamide, gliclazide, chlorpropamide, tolazamide, acetohexamide, glyclopyramide, glimepiride and the like) and other insulin secretagogues (e.g., repaglinide, senaglinide, mitiglinide or its calcium salt hydrate, GLP-1, nateglinide and the like), dipeptidylpeptidase IV inhibitors (e.g., NVP-DPP-278, PT-100, P32/98, LAF237 and the like), β3 agonists (e.g., CL-316243, SR-58611-A, UL-TG-307, AJ-9677, AZ40140 and the like), GLP-1 receptor agonists [e.g., GLP-1, NN-2211, AC-2993 (exendin-4), BIM-51077, Aib(8,35) hGLP-1 (7,37)NH$_2$ and the like], amylin agonists (e.g., pramlintide and the like), phosphotyrosine phosphatase inhibitors (e.g., vanadic acid and the like), gluconeogenesis inhibitors (e.g., glycogen phosphorylase inhibitors, glucose-6-phosphatase inhibitors, glucagon antagonists and the like), SGLT (sodium-glucose cotransporter) inhibitors (e.g., T-1095 and the like), and the like can be mentioned.

As the therapeutic agent for diabetic complications, is aldose reductase inhibitors (e.g., tolrestat, epalrestat, zenarestat, zopolrestat, fidarestat (SNK-860), minalrestat (ARI-509), CT-112 and the like), neurotrophic factors (e.g., NGF, NT-3 and the like), AGE inhibitors (e.g., ALT-945, pimagedine, pyratoxathine, N-phenacylthiazolium bromide (ALT-766), EXO-226 and the like), active oxygen scavengers (e.g., thioctic acid and the like), cerebral vasodilators (e.g., tiopuride and the like) and the like can be mentioned.

As the therapeutic agent for hyperlipidemia, statin compounds which are cholesterol synthesis inhibitors (e.g., pravastatin, simvastatin, lovastatin, atorvastatin, fluvastatin, cerivastatin or salts thereof (e.g., sodium salt and the like) and the like), squalene synthase inhibitors (e.g., compounds described in WO97/10224, for example, N-[[(3R,5S)-1-(3-acetoxy-2,2-dimethylpropyl)-7-chloro-5-(2, 3-dimethoxyphenyl)-2-oxo-1,2,3,5-tetrahydro-4,1-benzoxazepin-3-yl] acetyl]piperidine-4-acetic acid and the like), fibrate compounds possessing tryglyceride-decreasing action (e.g., bezafibrate, clofibrate, simfibrate, clinofibrate and the like) and the like can be mentioned.

As the hypotensive agent, angiotensin converting enzyme inhibitors (e.g., captopril, enalapril, delapril and the like), angiotensin II antagonists (e.g., losartan, candesartan cilexetil and the like), calcium antagonists (e.g., manidipine, nifedipine, amlodipine, efonidipine, nicardipine and the like), clonidine and the like can be mentioned.

As examples of the antiobesity agent, antiobesity drugs acting on the central nervous system (e.g., dexfenfluramine, fenfluramine, phentermine, sibutramine, anfepramon, dexamphetamine, mazindol, phenylpropanolamine, clobenzorex; MCH receptor antagonists (e.g., SB-568849; SNAP-7941; compounds included in WO01/82925 and WO01/87834; and the like); neuropeptide Y antagonists (e.g., CP-422935 and the like); cannabinoid receptor antagonists (e.g., SR-141716, SR-147778 and the like); ghrelin antagonists; 11β-hydroxysteroid dehydrogenase inhibitors (e.g., BVT-3498 and the like) and the like), pancreatic lipase inhibitors (e.g., orlistat, ALT-962 and the like), β3 agonists (e.g., CL-316243, SR-58611-A, UL-TG-307, AJ-9677, AZ40140 and the like), anorectic peptides (e.g., leptin, CNTF (ciliary neurotrophic factor) and the like), cholecystokinin agonists (e.g., lintitript, FPL-15849 and the like) and the like can be mentioned.

As examples of the diuretic, xanthine derivatives (e.g., sodium salicylate theobromine, calcium salicylate theobromine and the like), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide and the like), anti-aldosterone preparations (e.g., spironolactone, triamterene and the like), carbonate dehydratase inhibitors (e.g., acetazolamide and the like), chlorobenzenesulfonamide preparations (e.g., chlorthalidone, mefruside, indapamide and the like), azosemide, isosorbide, ethacrynic acid, piretanide, bumetanide, furosemide and the like can be mentioned.

As examples of the chemotherapeutic agent, alkylating agents (e.g., cyclophosphamide, ifosfamide and the like), metabolic antagonists (e.g., methotrexate, 5-fluorouracil or its derivatives, and the like), antitumor antibiotics (e.g., mitomycin, adriamycin and the like), plant-derived antitumor agents (e.g., vincristine, vindesine, Taxol and the like), cisplatin, carboplatin, etoposide and the like can be mentioned. Of these, 5-fluorouracil derivatives such as Furtulon and Neo-Furtulon are preferable.

As examples of the immunotherapeutic agent, microbial or bacterial components (e.g., muramyl dipeptide derivatives, Picibanil and the like), polysaccharides possessing immunopotentiator activity (e.g., lentinan, schizophyllan, krestin and the like), cytokines obtained by gene engineering technology (e.g., interferons, interleukins (IL) and the like), colony stimulating factors (e.g., granulocyte colony stimulating factor, erythropoietin and the like) and the like can be mentioned; of these, interleukins such as IL-1, IL-2 and IL-12 are preferable.

As examples of the cachexia ameliorator, cyclooxygenase inhibitors (e.g., indomethacin and the like) [Cancer Research, vol. 49, pp. 5935-5939, 1989], progesterone derivatives (e.g., megestrol acetate) [Journal of Clinical Oncology, vol. 12, pp. 213-225, 1994], glucocorticoids (e.g., dexamethasone and the like), metoclopramide pharmaceuticals, tetrahydrocannabinol pharmaceuticals (references are the same as the above-mentioned ones), fat metabolism ameliorators (e.g., eicosapentaenoic acid and the like) [British Journal of Cancer, vol. 68, pp. 314-318, 1993], growth hormones, IGF-1, antibodies against the cachexia-inducing factor TNF-α, LIF, IL-6 or oncostatin M, and the like, can be mentioned.

As examples of the agent acting on peripheral and central nerves, acetylcholine esterase inhibitors (e.g., tacrine, donepezil, rivastigmin, galanthamine and the like), dopamine receptor agonists (e.g., L-dopa, apomorphine and the like), monoamine uptake inhibitors (e.g., tramadol), GABA receptor agonists (e.g., Gabapentin), acetylcholine receptor ligands (e.g., ABT-594), muscarinic acetylcholine receptor agonists (e.g., Arecoline-DDS), nicotinic acetylcholine receptor agonists (e.g., GTS-21), AMPA receptor agonists (e.g., AMPALEX), monoamine oxidase inhibitors (e.g., ELDEPRYLTDS), amyloid β protein secretion/coagulation inhibitors (e.g., ALZHEMED), nerve differentiation/regeneration promoters (e.g., Xaliproden), therapeutic drugs for cerebrovascular dementia (e.g., Memantine), therapeutic drugs for transient cerebral ischemic attack (e.g., PLAVIX), antioxidants (e.g., RADICUT), glutamic acid antagonists (e.g., MAXIPROST), therapeutic drugs for bipolar disorder (e.g., sodium valproate), therapeutic drugs for schizophrenia (e.g., Olanzapine), COMT inhibitors (e.g., Tolcapone) and the like can be mentioned.

As example of the therapeutic agent for ulcers, prostaglandin preparations (e.g., prostaglandin E1), growth factor preparations (e.g., PDGF) and the like can be mentioned.

As examples of the anti-inflammatory agent, antirheumatic drugs (e.g., leflunomide), non-steroidal anti-inflammatory drugs (e.g., aspirin, acetaminophen, indomethacin), COX-2 inhibitors (e.g., VIOXX) and the like can be mentioned.

Furthermore, glycation inhibitors (e.g., ALT-711 and the like), nerve regeneration promoters (e.g., Y-128, VX853, prosaptide and the like), antidepressants (e.g., desipramine, amitriptyline, imipramine), antiepileptics (e.g., lamotrigine), antiarrhythmics (e.g., mexiletine), endothelin receptor antagonists (e.g., ABT-627), narcotic analgesics (e.g., morphine), α2 receptor agonists (e.g., clonidine), focal analgesics (e.g., capsaicin), protein kinase C inhibitors (e.g., LY-333531), antianxiety drugs (e.g., benzodiazepine), phosphodiesterase inhibitors (e.g., sildenafil), therapeutic agents for osteoporosis (e.g., alfacalcidol, calcitriol, elcatonin, salmon calcitonin, estriol, ipriflavone, disodium pamidronate, sodium alendronate hydrate, disodium incadronate and the like), therapeutic agents for urinary incontinence or pollakiuria (e.g., flavoxate hydrochloride, oxybutynin hydrochloride, propiverine hydrochloride and the like), vitamins (e.g., vitamin B1, vitamin B12), creatine, calnitin, aminoethylsulfonic acid (Taurin (trade name)) and the like can be also used in combination with the agent of the present invention.

By using the agent of the present invention and the aforementioned concomitant drug in combination, excellent effects, for example, an effect to enhance the action of the agent of the present invention or the concomitant drug; an effect to reduce the dose of the agent of the present invention or the concomitant drug; an effect to reduce the side effects of the agent of the present invention or the concomitant drug; and the like, can be obtained.

The concomitant drug is preferably an insulin preparation, an insulin sensitizer, an a-glucosidase inhibitor, a biguanide agent, an insulin secretagogue, an aldose reductase inhibitor, a non-steroidal anti-inflammatory drug, an antidepressant and the like.

The present invention further relates to an agent for the prophylaxis or treatment of Down's syndrome comprising a VDAC regulator.

Here, the VDAC regulator means a drug that regulates (normalizes by promotion or inhibition) a VDAC function, and may be any of a peptide, protein, and non-peptide compound. Here, as examples of VDAC, VDAC-1, VDAC-2, VDAC-3 and the like can be mentioned. As the VDAC function, transportation of solutes involved in energy production in mitochondria, glycolipid metabolism, apoptosis, intracellular Ca homeostasis and the like; interaction with factors such as hexokinase and Bax; and the like can be mentioned.

The VDAC regulator is preferably a non-peptide compound; as specific examples thereof, Compound (I), a salt thereof or a prodrug thereof and the like mentioned above can be mentioned. Also, the VDAC regulator is preferably a drug that inhibits the aforementioned VDAC function.

The VDAC regulator is low in toxicity and can be administered safely to mammals (e.g., humans, mice, rats, rabbits, dogs, cats, bovines, horses, swines, monkeys, and the like).

The agent for the prophylaxis or treatment of Down's syndrome of the present invention can generally be formulated into a preparation in the same manner as the aforementioned agent of the present invention using the VDAC regulator and a pharmacologically acceptable carrier, and its dosage form is the same as the case of the agent of the present invention. Also, the agent for the prophylaxis or treatment of Down's syndrome can also be used in combination with the aforementioned various concomitant drugs.

Although the dose of the agent for the prophylaxis or treatment of Down's syndrome of the present invention varies depending on administration subject, route of administration, symptoms and the like, when said agent for the prophylaxis or treatment is orally administered to an adult, its dose as the amount of the VDAC regulator, which is the active ingredient, per dose, is generally about 0.05 to 500 mg/kg body weight, preferably about 0.5 to 100 mg/kg body weight. It is desirable that this dose be administered once to three times a day.

The present invention further relates to a method for screening an agent for the prophylaxis or treatment of a nervous system disease, which comprises using VDAC (hereinafter sometimes abbreviated as the screening method of the present invention).

Here, as examples of VDAC, VDAC-1, VDAC-2, VDAC-3 and the like can be mentioned. Also, as nervous system diseases, the same as those mentioned above can be mentioned. Of these, diabetic neuropathy and amyotrophic lateral sclerosis are preferable, with preference given to diabetic neuropathy.

The screening method of the present invention is carried out specifically by:

1) determining the binding ability of a test compound to VDAC;
2) comparing a VDAC function between in the presence and in the absence of a test compound; and the like.

The VDAC used in the screening method of the present invention may be derived from any of mammalian (e.g., humans, mice, rats, rabbits, dogs, cats, bovines, horses, swines, monkeys and the like) cells (for example, hepatocytes, splenocytes, neurocytes, glial cells, pancreatic β cells, myelocytes, mesangial cells, Langerhans' cells, epidermal cells, epithelial cells, goblet cells, endothelial cells, smooth muscle cells, fibroblasts, fibrocytes, myocytes, adipocytes, immunocytes (e.g., macrophages, T cells, B cells, natural killer cells, mast cells, neutrophils, basophils, eosinophils, monocytes), megakaryocytes, synovial cells, chondrocytes, osteocytes, osteoblasts, osteoclasts, mammary gland cells, hepatocytes or interstitial cells, or precursor cells, stem cells or cancer cells of these cells, and the like) or all tissues in which these cells are present, for example, brain, various portions of brain (e.g., olfactory bulb, amygdala, basal ganglion, hippocampus, thalamus, hypothalamus, cerebral cortex, medulla oblongata, cerebellum), spinal cord, pituitary, stomach, pancreas, kidney, liver, gonads, thyroid, gallbladder, bone marrow, adrenal, skin, muscles, lung, gastrointestinal tract (e.g., large intestine, small intestine), blood vessels, heart, thymus, spleen, submandibular gland, peripheral blood, prostate, testis, ovary, placenta, uterus, bone, joints, skeletal muscles, and the like.

VDAC can be obtained from the aforementioned mammalian cells or tissues, using a protein purification method known per se. Specifically, by homogenizing a mammalian tissue or cells, and separating and purifying the soluble fraction by chromatographies such as reversed-phase chromatography and ion exchange chromatography, VDAC can be obtained.

Also, VDAC can also be produced according to a known peptide synthesis method.

As examples of the test compound, peptides, proteins, non-peptide compounds, fermentation products, cell extract, plant extract, animal tissue extract and the like can be mentioned; these may be any of novel compounds or known compounds.

The binding ability of the test compound to VDAC can, for example, be determined by binding the marker-labeled test compound to mitochondria isolated from mammalian tissue, in the presence or absence of an unlabeled test compound, determining the radioactivity of the mitochondria after washing using a method known per se, and calculating specific binding.

Also, the binding ability of the test compound to VDAC can also be determined by binding the marker-labeled test compound to purified VDAC or VDAC incorporated in a lipid membrane, in the presence or absence of an unlabeled test compound, carrying out ultrafiltration, determining the radioactivity of the ultrafiltration membrane after washing using a method known per se, and calculating specific binding. Here, in place of ultrafiltration, filtration using a material that adsorbs protein, such as a glass filter, may be carried out.

As examples of the aforementioned markers, isotopes (e.g., $^3H$, $^{14}C$ and the like) and the like can be mentioned.

In the above-described screening method, the test compound that binds to VDAC, that is, a compound that inhibits VDAC, is useful as an-agent for the prophylaxis or treatment of a nervous system disease.

As VDAC functions, those mentioned above can be mentioned, and said functions can, for example, be determined by examining whether or not the index substance can pass VDAC. Said index substance may be any one, as long as it is capable of passing VDAC; as specific examples thereof, sucrose, cytochrome c and the like, labeled with an isotope (e.g., $^3H$, $^{14}C$, and the like), can be mentioned.

The screening method which comprises comparing a VDAC function can, for example, be carried out by culturing cells having VDAC, in the co-presence of an index substance and in the presence or absence of the test compound, and then determining the amount of the index substance accumulated in the cells.

As cells having VDAC, the aforementioned mammalian cells can be mentioned.

As media for the cultivation of the cells, for example, a MEM medium containing about 5 to 20% fetal calf serum [Science, vol. 122, 501 (1952)], DMEM medium [Virology, vol. 8, 396 (1959)], RPMI 1640 medium [The Journal of the American Medical Association, vol. 199, 519 (1967)], 199 medium [Proceeding of the Society for the Biological Medicine, vol. 73, 1 (1950)] and the like can be used. The pH of the medium is preferably about 6 to 8. Cultivation is carried out generally at about 30° C. to 40° C. for about 0.1 to 96 hours (preferably about 0.5 to 48 hours). Aeration and stirring may be carried out as necessary.

Determination of the amount of the index substance is carried out using a known assay kit and the like according to a method known per se.

In the above-described screening method, a compound that regulates (promotes or inhibits) a VDAC function, particularly a compound that inhibits a VDAC function, is useful as an agent for the prophylaxis or treatment of a nervous system disease.

For example, a test compound that increases a VDAC function by about 20% or more, preferably 30% or more, more preferably about 50% or more, as a compound that promotes a VDAC function; and a test compound that decreases a VDAC function by about 20% or more, preferably 30% or more, more preferably about 50% or more, as a compound that inhibits a VDAC function, can be selected respectively.

The present invention further relates to a "method for preventing or treating a nervous system disease in a mammal, which comprises administering a VDAC regulator to said mammal".

As examples of the mammal, humans, mice, rats, rabbits, dogs, cats, bovines, horses, swines, monkeys and the like can be mentioned.

As the VDAC regulator, those mentioned as the active ingredient in the aforementioned agent for the prophylaxis or treatment of Down's syndrome can be mentioned.

As the nervous system disease, the same as those mentioned above can be mentioned. Of these, diabetic neuropathy and amyotrophic lateral sclerosis are preferable, with preference given to diabetic neuropathy.

The VDAC regulator is low in toxicity and can be administered safely to mammal.

The VDAC regulator can generally be formulated into a preparation in the same manner as the aforementioned agent for the prophylaxis or treatment of Down's syndrome using a pharmacologically acceptable carrier, and its dosage form, dose and the like are the same as the case of the agent for the prophylaxis or treatment of Down's syndrome. Also, the VDAC regulator can also be used in combination with the aforementioned various concomitant drugs.

The present invention is hereinafter described in more detail by means of examples, reference examples and experimental examples but is not limited thereby.

As the various pharmaceutical materials used in the examples, items complying with the Japanese Pharmacopoeia XIV were used.

EXAMPLES

Example 1

Production of Capsules

| | |
|---|---|
| 1) Compound (5) | 30 mg |
| 2) Finely divided cellulose | 10 mg |
| 3) Lactose | 19 mg |
| 4) Magnesium stearate | 1 mg |
| Total | 60 mg |

1), 2), 3) and 4) are admixed and filled into a gelatin capsule.

Example 2

Production of Tablets

| | |
|---|---|
| 1) Compound (5) | 30 g |
| 2) Lactose | 50 g |
| 3) Cornstarch | 15 g |
| 4) Carboxymethylcellulose calcium | 44 g |
| 5) Magnesium stearate | 1 g |
| 1000 tablets | 140 g |

The whole amounts of 1), 2) and 3) and 30 g of 4) are kneaded with water; after vacuum drying, granulation is carried out. This granular mixture is admixed with 14 g of 4) and 1 g of 5) and the resulting mixture is tableted using a tableting machine. 1000 tablets containing 30 mg of Compound (5) per tablet are obtained.

Example 3

Production of Capsules

| | |
|---|---|
| 1) Compound (5) | 30 mg |
| 2) Finely divided cellulose | 10 mg |
| 3) Lactose | 19 mg |
| 4) Magnesium stearate | 1 mg |
| Total | 60 mg |

1), 2), 3) and 4) are admixed and filled into a gelatin capsule.

Example 4

Production of Tablets

| | |
|---|---|
| 1) Compound (5) | 30 g |
| 2) Lactose | 50 g |
| 3) Cornstarch | 15 g |
| 4) Carboxymethylcellulose calcium | 44 g |
| 5) Magnesium stearate | 1 g |
| 1000 tablets | 140 g |

The whole amounts of 1), 2) and 3) and 30 g of 4) are kneaded with water; after vacuum drying, granulation is carried out. This granular mixture is admixed with 14 g of 4) and 1 g of 5) and the resulting mixture is tableted using a tableting machine. 1000 tablets containing 30 mg of Compound (5) per tablet are obtained.

Example 5

Production of Film-coated Tablets

[Production of a Coating Agent]

209.6 g of hydroxypropylmethylcellulose 2910 (TC-5) and 42.0 g of Macrogol 6000 (polyethylene glycol 6000) were dissolved in 2520 g of purified water. In the obtained solution, 28.0 g of titanium oxide and 0.4 g of yellow iron sesquioxide were dispersed, to give a coating agent.

[Production of Plain Tablets]

After 62.5 g of Compound (5), 3738 g of lactose and 750.0 g of cornstarch were admixed uniformly in a fluidized-bed granulating dryer (FD-5S, POWREX Corporation), granulation was carried out in the dryer, while spraying an aqueous solution of 150 g of hydroxypropylcellulose (HPC-L) dissolved therein, and subsequently drying was carried out in the fluidized-bed granulating dryer.

The obtained granules were crushed with a 1.5 mmφ punching screen using a Power-Mill pulverizer (P-3, Showa Machinery Co., Ltd.) to yield a pulverized powder.

To 4136 g of the obtained pulverized powder, 220 g of croscarmellose sodium and 44 g of magnesium stearate were added, and these were admixed in a tumbler mixer (TM-15, Showa Machinery Co., Ltd.) to yield granules for tableting. The obtained granules were tableted (tableting pressure: 7KN/punch) at 200 mg weight with a 8.5 mm φ punching screen using a rotary tableting machine (Correct 19K, Kikusui Seisakusho Co., Ltd.).

[Production of Film-coated Tablets]

The aforementioned coating agent was sprayed onto the obtained plain tablets in a Driacoater coating machine (DRC-500, manufactured by POWREX) to give 19000 film-coated tablets of the following prescription containing 2.5 mg of Compound (5) per tablet.

Prescription of Plain Tablets (Composition per Tablet)

| | |
|---|---|
| 1) Compound (5) | 2.5 mg |
| 2) Lactose | 149.5 mg |
| 3) Cornstarch | 30.0 mg |
| 4) Croscarmellose sodium | 10.0 mg |

-continued

| | | |
|---|---|---|
| 5) Hydroxypropylcellulose | 6.0 mg | |
| 6) Magnesium stearate | 2.0 mg | |
| Total | 200.0 mg | |

Prescription of Film-coated Tablets (Composition per Tablet)

| | |
|---|---|
| 1) Plain tablet (Film ingredients) | 200.0 mg |
| 2) Hydroxypropylmethylcellulose 2910 | 5.24 mg |
| 3) Macrogol 6000 | 1.05 mg |
| 4) Titanium oxide | 0.7 mg |
| 5) Yellow iron sesquioxide | 0.01 mg |
| Total | 207.0 mg |

Example 6

Production of Film-coated Tablets

In the same manner as in Example 5, except that the amounts of Compound (5) and lactose used were 375.0 g and 3425 g, respectively, 19000 film-coated tablets of the following prescription containing 15 mg of Compound (5) per tablet were obtained.

Prescription of Plain Tablets (Composition per Tablet)

| | |
|---|---|
| 1) Compound (5) | 15.0 mg |
| 2) Lactose | 137.0 mg |
| 3) Cornstarch | 30.0 mg |
| 4) Croscarmellose sodium | 10.0 mg |
| 5) Hydroxypropylcellulose | 6.0 mg |
| 6) Magnesium stearate | 2.0 mg |
| Total | 200.0 mg |

Prescription of Film-coated Tablets (Composition per Tablet)

| | |
|---|---|
| 1) Plain tablet (Film ingredients) | 200.0 mg |
| 2) Hydroxypropylmethylcellulose 2910 | 5.24 mg |
| 3) Macrogol 6000 | 1.05 mg |
| 4) Titanium oxide | 0.7 mg |
| 5) Yellow iron sesquioxide | 0.01 mg |
| Total | 207.0 mg |

Example 7

Production of Film-coated Tablets

In the same manner as in Example 5, except that the amounts of Compound (5) and lactose used were 1500.0 g and 2300 g, respectively, 19000 film-coated tablets of the following prescription containing 60 mg of Compound (5) per tablet were obtained.

Prescription of Plain Tablets (Composition per Tablet)

| | |
|---|---|
| 1) Compound (5) | 60.0 mg |
| 2) Lactose | 92.0 mg |
| 3) Cornstarch | 30.0 mg |
| 4) Croscarmellose sodium | 10.0 mg |
| 5) Hydroxypropylcellulose | 6.0 mg |
| 6) Magnesium stearate | 2.0 mg |
| Total | 200.0 mg |

Prescription of Film-coated Tablets (Composition per Tablet)

| | |
|---|---|
| 1) Plain tablet (Film ingredients) | 200.0 mg |
| 2) Hydroxypropylmethylcellulose 2910 | 5.24 mg |
| 3) Macrogol 6000 | 1.05 mg |
| 4) Titanium oxide | 0.7 mg |
| 5) Yellow iron sesquioxide | 0.01 mg |
| Total | 207.0 mg |

Reference Example 1

Production Example of Carboxyl Group-type Latex Particles

Latex particles produced according to the method described in Japan Patent No. 3086427 (JP-B-3086427) (SG-EGDE particles) were subjected to ammonia treatment to thereby cleave the surface epoxy group and introduce an amino group. After the obtained particles were washed with water, they were dispersed in dimethylformamide, and triethylamine of 10% volume and an excess amount of succinic anhydride were added. The obtained mixture was stirred at normal temperature for 12 hours or more to introduce a carboxyl group to the amino group moiety of the particle surface, to thereby produce carboxyl group-type latex particles.

Reference Example 2

Production Example of Compound A

A mixture of 3-[4-(4-chlorophenyl)-2-(2-methyl-1-imidazolyl)-5-oxazolyl]propyl methanesulfonate (395 mg), methyl 4-hydroxybenzoate (225 mg), potassium carbonate (276 mg) and N,N-dimethylformamide (10 ml) was stirred at 90° C. for 2 hours. The reaction mixture was poured into water and extracted with ethyl acetate. The organic layer was washed with saturated brine, dried over anhydrous magnesium sulfate, and concentrated. The obtained yellow oily substance was dissolved in tetrahydrofuran (30 ml), lithium aluminum hydride (80 mg) was added little by little at 0° C., and stirring was carried out at 0° C. for 1 hour. To the reaction mixture, sodium sulfate decahydrate (1.0 g) was added, and stirring was carried out at room temperature for 30 minutes, after which filtration was carried out. The filtrate was concentrated and the residue was purified by silica gel column chromatography. From the fraction eluted with ethyl acetate, 4-({3-[4-(4-chlorophenyl)-2-(2-methyl-1-imidazolyl)-5-oxazolyl]propyl}oxy)benzyl alcohol (304 mg, yield 72%) was obtained as a colorless oily substance.

NMR (CDCl$_3$): δ1.77 (1H, t, J=5.5 Hz), 2.15-2.3(2H, m) 2.73 (3H, s), 3.15(2H, t, J=7 Hz), 4.04(2H, t, J=7 Hz), 4.61 (2H, d, J=5.5 Hz), 6.82 (2H, d, J=9 Hz), 6.97(1H, d, J=1.5

Hz), 7.26 (2H, d, J=9 Hz), 7.34 (2 H, d, J=9 Hz), 7.41 (1H, d, J=1.5 Hz), 7.60 (2H, d, J=9 Hz).

A mixture of 4-({3-[4-(4-chlorophenyl)-2-(2-methyl-1-imidazolyl)-5-oxazolyl]propyl}oxy)benzyl alcohol (1.90 g), thionyl chloride (0.95 g) and tetrahydrofuran (10 ml) was stirred at room temperature for 3 hours. The reaction mixture was concentrated, poured into water, and extracted with ethyl acetate. The ethyl acetate layer was washed with saturated brine, dried over anhydrous magnesium sulfate, and concentrated. The residue was dissolved in N,N-dimethylformamide (10 ml), sodium diformylimide (1.0 g) was added, and the solution was stirred at 60° C. overnight. The reaction mixture was poured into water and extracted with ethyl acetate. The ethyl acetate layer was washed with saturated brine, dried over anhydrous magnesium sulfate, and concentrated. After the residue was subjected to silica gel flush chromatography, the obtained fraction was concentrated. The obtained oily substance was dissolved in a mixture of 4N hydrochloric acid-acetic acid solution (10 ml) and ethanol (30 ml) and stirred overnight. The reaction mixture was concentrated and the obtained solid was recrystallized from ethanol-diethyl ether to give 4-{3-[4-(4-chlorophenyl)-2-(2-methyl-1-imidazolyl)-5-oxazolyl]propyloxy}benzylamine dihydrochloride (containing 0.25 molecules of ethanol and 1 molecule of water per molecule of the compound) (herein sometimes abbreviated as Compound A) as a hygroscopic colorless prism crystal (750 mg, 32%).

Elemental analysis ($C_{23}H_{25}N_4O_2Cl_3$, 0.25 ethanol, $1H_2O$): Calcd.: C, 55.04; H, 6.77; N, 4.29 Found: C, 55.07; H, 6.92; N, 4.25.

Experimental Example 1

Identification of Compound (5)-Binding Protein

After 5 mg of carboxyl group-type latex particles obtained in Reference Example 1 was dispersed in dioxane, 23 mg of N-hydroxysuccinimide and 38 mg of water-soluble carbodiimide were added, and they were reacted at room temperature (about 20 to 25° C., the same applies below) for 2 hours. After the obtained succinimide-immobilized particles were washed with methanol, they were reacted with 4 mM Compound A (amino derivative of Compound (5)) in 0.5 mL of 0.2M sodium acetate buffer solution (pH 5.3) at room temperature for 1 hour to thereby immobilize Compound A onto the particles. To the obtained particles, 1M aqueous solution of ethanolamine-hydrochloric acid (pH 8.5) was added, and they were reacted at room temperature or 2 hours to thereby block unreacted groups in the succinimide-immobilized particles, after which the particles were washed with 50% methanol and water to give Compound A-immobilized particles. The Compound A-immobilized particles were dispersed in water to obtain a concentration of 10 mg/mL and stored under refrigeration.

In the meantime, protein was extracted from the nuclear fraction of human neuroblastoma SK-N-SH (ATCC) according to the method of Dignam, J. D. et al. (Nucleic Acids Res. 11, 1475-1489 (1983)), and dissolved in 0.05TGEMN (Tris-HCL/Glycerol/EDTA (ethylenediaminetetraacetic acid)/$MgCl_2$/NP-40) buffer [50 mM sodium chloride, 10 mM Tris-HCl (pH 7.5), 10% (w/v) glycerol, 0.2 mM EDTA, 1 mM $MgCl_2$, 0.1% NP-40 (Nonylphenoxy polyethoxy ethanol)] (containing as freshly added additives 0.5 mM DTT (Dithiothreitol), 0.5 mM APMSF (4-Amidinophenylmethanesulfonyl Fluoride), 1 µg/mL leupeptin, and 1 µg/mL pepstatin A) to obtain a concentration of 0.73 mg/mL. 0.15 mL of this protein solution and 0.3 mg of the aforementioned Compound A-immobilized particles were admixed and incubated at 4° C. for 3 hours to thereby bind the Compound A-binding protein to Compound A on the particle surface.

Subsequently, centrifugation (15, 000×g, 5 minutes) was carried out, the supernatant was removed, and the obtained particles were washed with 0.05TGEMN buffer. The particles after washing were dispersed in 0.1 mL of a 0.05TGEMN buffer containing 0.3 µL of DMF (FIG. 1, Lane 1) or in 0.1 mL of 0.05TGEMN buffer containing 300 µM Compound (5) and 0.3 µL of DMF (FIG. 1, Lane 2), and incubated at 4° C. for 1.5 hours. After centrifugation (15, 000×g, 5 minutes), the protein-containing supernatant was analyzed by SDS-PAGE.

Figure 1:
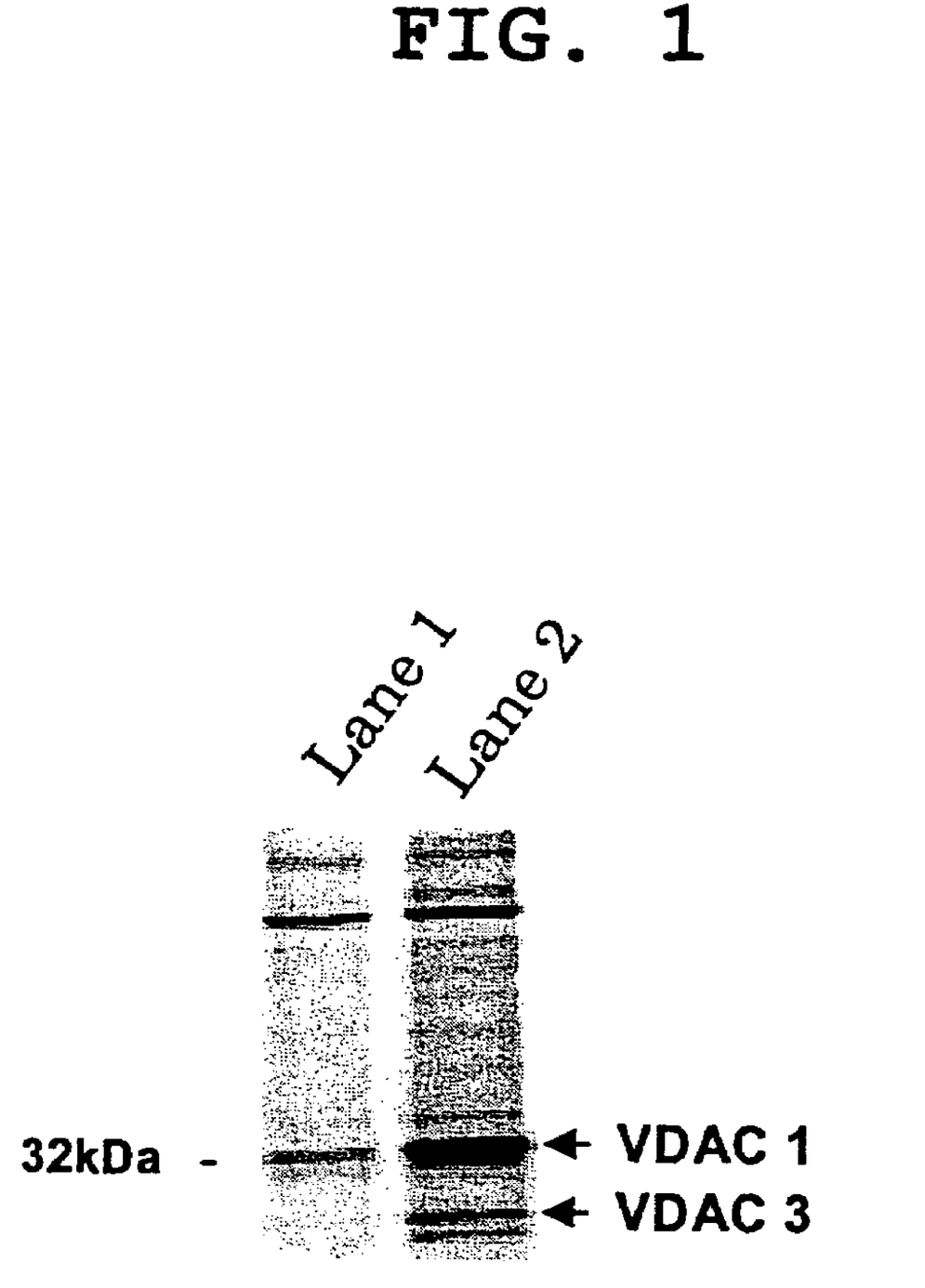
FIG. 1 shows the results of SDS-PAGE analysis of a protein eluted from human neuroblastoma-derived protein using Compound (5). In the figure, Lane 1 shows a protein band eluted with a buffer not containing Compound (5), and Lane 2 shows a protein band eluted with a buffer containing Compound (5).

The gel after SDS-PAGE was stained using a silver staining kit (Wako Pure Chemical), and an about 32 kDa protein band and about 30 kDa protein band, which were eluted selectively by Compound (5), were identified (FIG. 1).

Figure 2:
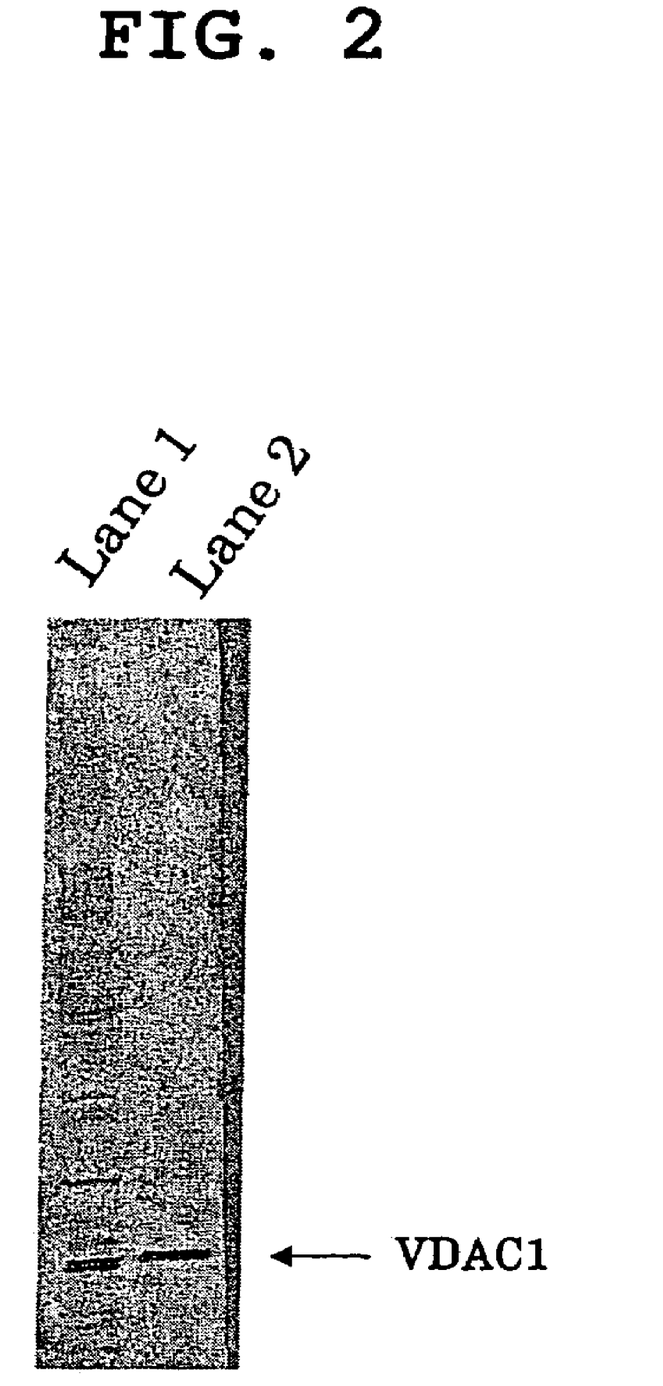
FIG. 2 shows the results of Western blotting with anti-VDAC1 antibody to detect an about 32 kDa protein band eluted from human neuroblastoma-derived protein using Compound (5). In the figure, Lane 1 shows a band of total protein, and Lane 2 shows a band of Compound (5)-binding protein.

The same SDS-PAGE procedures as those mentioned above were carried out, the obtained gel was stained with CBB (Coomassie Brilliant Blue), the desired band was cleaved out, and mass spectrometry (TOF-MS, Shimadzu Corporation) of the protein component in the gel was carried out. As a result, the above-described protein bands proved to correspond to voltage-dependent anion channel (VDAC)-1 and VDAC-3, respectively. Also, the about 32 kDa protein band was identified as VDAC-1 by the immunoblotting method described below (FIG. 2).

First, SK-N-SH cells (ATCC) were disrupted by ultrasonication in 0.1TGEMN buffer [100 mM sodium chloride, 10 mM Tris-HCl (pH 7.5), 10% (w/v) glycerol, 0.2 mM EDTA, 1 mM $MgCl_2$, 0.1% NP-40] (containing as freshly added additives 0.5 mM DTT, 0.5 mM APMSF, 1 µg/mL leupeptin, and 1 µg/mL pepstatin A) to give a 1.43 mg/mL protein solution. 0.1 mL of this protein solution was added to 0.3 mg of the aforementioned Compound A-immobilized particles in a 1.5 mL Eppendorf tube, and overnight incubation was carried out at 4° C., to thereby bind the Compound A-binding protein to Compound A on the particle surface.

After centrifugation (15,000×g, 5 minutes), the supernatant was removed and the obtained particles were washed with 0.1TGEMN buffer three times. Each of a suspension of the particles after washing in SDS-PAGE buffer (New England Biolabs) (97.5 µL) (FIG. 2, Lane 2) and a mixed solution of 5 µL of the above-described protein solution and 10 µL of SDS-PAGE buffer (FIG. 2, Lane 1) was boiled for 5 minutes. After each of the suspension and the mixed solution was centrifuged at 15,000 rpm for 5 minutes, 15 µL of the supernatant was electrophoresed. After electrophoresis, the obtained gel was Western-blotted onto a nylon membrane according to a conventional method, and using anti-Porin 31HL antibody (529536, Calbiochem), previously diluted to 5 µg/mL, secondary antibody (anti-mouse IgG-AP conjugated, Bio-Rad), previously diluted 5000 fold, and NBT/BCIP detection fluid (Promega), band detection was carried out.

Experimental Example 2

Cytochrome c Leakage Suppressing Action

The effect of Compound (5) on VDAC function was evaluated by determining the amount of cytochrome c leakage in the cytoplasm of PC12 cells.

PC12 cells, pre-cultured in a DMEM (Dulbecco's Modified Eagle's Medium) containing 10% FCS (Fetal Calf Serum), were sown to a culture dish of 10 cm diameter (Falcon) and cultured until they became nearly confluent. After the culture dish was washed with DMEM, a DMEM containing 0.5% FCS (0.5% FCS group) or a DMEM containing 0.5% FCS and 0.3 µmol/L Compound (5) (0.5% FCS+Compound (5) group) was added, and the cells were further cultured for 16 hours. The cells suspended in the culture broth and the cells adhering to the culture dish, detached by trypsin-EDTA treatment, were recovered. The recovered cells, after being washed with PBS, were ice-cooled in a digitonin solution [10 mmol/L HEPES, 0.3 mol/L mannitol, 0.1% (w/v) BSA, 100 µmol/L digitonin] (100 µL) for 5 minutes to extract cytoplasmic protein. After the obtained cytoplasmic protein was centrifuged at 8500×g for 5 minutes, 12 µL of the supernatant was analyzed using an assay kit [cytochrome c ELISA kit (MBL) and BCL-II (Pierce), respectively] to determine its cytochrome c content and protein content. Subsequently, the cytochrome c content per unit amount of total protein was calculated, and this was taken as the amount of cytochrome c leakage (ng/mg). The results are shown in [Table 1].

TABLE 1

|  | Amount of cytochrome c leakage (ng/mg) |
|---|---|
| 0.5% FCS group | 19.4 |
| 0.5% FCS + Compound (5) group | 7.0 |

As shown above, it was proven that Compound (5) decreased the amount of cytochrome c leakage. That is, Compound (5) suppressed the cytochrome c leakage action, which is a function of VDAC.

Experimental Example 3

The apoptosis-suppressing action of Compound (5) was evaluated by determining the nucleosome content in PC12 cells.

PC12 cells, pre-cultured in a DMEM containing 10% FCS, were sown to a 24-well culture plate to obtain a concentration of $6 \times 10^4$ cells/well, and cultured for 24 hours. After the culture plate was washed with DMEM, a DMEM containing 0.5% FCS (0.5% FCS group) or a DMEM containing 0.5% FCS and 0.3 µmol/L Compound (5) (0.5% FCS+Compound (5) group) was added, and the cells were further cultured for 24 hours. Also, as a control group, the same procedures were carried out using a DMEM containing 10% FCS (10% FCS group). The cells suspended in the culture broth and the cells adhering to the culture plate, detached by trypsin-EDTA treatment, were recovered. According to the protocol of an apoptosis assay kit with nucleosome detection as an index (Cell Death Detection ELISA, Roche), the recovered cells were suspended in 500 µL of the cytolytic solution attached to said assay kit. After the suspension was ice-cooled for 30 minutes, it was centrifuged at 15,000 rpm for 10 minutes and 400 µL of the supernatant was recovered. Said supernatant was diluted 2 fold and subjected to ELISA to determine its nucleosome content. Subsequently, taking the nucleosome content in the 10% FCS group as 100%, percentage in each group was calculated. The results are shown in [Table 2].

TABLE 2

|  | Nucleosome content (%) |
|---|---|
| 10% FCS group | 100 |
| 0.5% FCS group | 422 |
| 0.5% FCS + Compound (5) group | 176 |

As shown above, it was proven that the nucleosome content increased as the FCS concentration during cell culture decreased from 10% to 0.5%, and that this increase was suppressed by Compound (5). That is, Compound (5) suppressed low serum-induced apoptosis.

Experimental Example 4

The mitochondria respiration activity-increasing action of Compound (5) was evaluated using Alamar Blue.

After PC12 cells, pre-cultured in a DMEM containing 10% fetal calf serum (FCS), were suspended in the same medium to obtain a concentration of $2 \times 10^5$ cells/mL, the obtained suspension was sown to a 96-well culture plate to obtain a concentration of 0.1 mL/well and cultured for 24 hours. After said culture plate was washed with DMEM, a solution obtained by diluting Compound (5) in FCS-free DMEM to obtain a concentration of 3 µmol/L was added, and cultivation was carried out for 3 hours [Compound (5) addition group].

In the meantime, PC12 cells were cultured in the same manner, except that Compound (5) was not added [Compound (5) non-addition group], or B-27 (trade name, Life Science), which is a supplement for nerve culture was added at a concentration of 10% in place of the solution of Compound (5) [B-27 addition group].

Subsequently, to each well of the culture plate, 10 µL of Alamar Blue solution (Alamar Biosciences), which is a mitochondria respiration activity indicator, was added; fluorescence just after the addition and after the plate was allowed to stand in a 5% $CO_2$ incubator at 37° C. for 10 minutes was determined using a Fluoroscan (Flow Laboratories) [excitation wavelength (Ex.): 538 nm, emission wavelength (Em.): 590 nm], and its variation was obtained.

Furthermore, taking the fluorescence variation in the B-27 addition group as 100%, relative values of fluorescence variation in the Compound (5) addition group and the Compound (5) non-addition group were calculated.

As a result, the fluorescence variation increased to 126.7%±15.7% (mean±standard deviation, n=7) in the Compound (5) addition group and decreased to 73.2%±1.9% (mean±standard deviation, n=7) in the Compound (5) non-addition group. Also, the fluorescence variation in the Compound (5) addition group increased significantly (p<0.001, t-test) compared to the fluorescence variation in the Compound (5) non-addition group. This demonstrated that Compound (5) possesses mitochondria respiration activity-increasing action.

Experimental Example 5

The mitochondria membrane potential-stabilizing action of Compound (5) was evaluated using Rodamin 123 (trade name, Molecular Probe).

After PC12 cells, pre-cultured in a DMEM containing 10% fetal calf serum (FCS), were suspended in the same medium to obtain a concentration of $2 \times 10^5$ cells/mL, the obtained suspension was sown to a 96-well culture plate to obtain a concentration of 0.1 mL/well and cultured for 24 hours. After said culture-plate was washed with DMEM, a solution obtained by diluting Compound (5) in FCS-free DMEM to obtain a concentration of 3 µmol/L was added, and cultivation was carried out for 4 hours [Compound (5) addition group].

In the meantime, PC12 cells were cultured in the same manner, except that Compound (5) was not added [Com pound (5) non-addition group], or 10% FCS was added in place of the solution of Compound (5) [FCS addition group].

Subsequently, to each well of the culture plate, Rodamin 123 (trade name, Molecular Probe), which is a mitochondria membrane potential indicator, was added to obtain a concentration of 1 μmol/L; fluorescence just after the addition and after the plate was allowed to stand in a 5% $CO_2$ incubator at 37° C. for 10 minutes was determined using a Fluoroscan (Flow Laboratories) [excitation wavelength (Ex.): 485 nm, emission wavelength (Em.): 538 nm], and its variation was obtained.

Furthermore, taking the fluorescence variation in the FCS addition group as 100%, relative values of fluorescence variation in the Compound (5) addition group and the Compound (5) non-addition group were calculated.

As a result, the fluorescence variation rose abnormally to 131.2±12.9% (mean±standard deviation, n=8) in the Compound (5) non-addition group but it showed only a slight rise to 110.0%±8.0% (mean±standard deviation, n=8) in the Compound (5) addition group. Also, the fluorescence variation in the Compound (5) addition group decreased significantly (p<0.001, t-test) compared to the fluorescence variation in the Compound (5) non-addition group. This demonstrated that Compound (5) possesses mitochondria membrane potential-stabilizing action.

INDUSTRIAL APPLICABILITY

The VDAC regulator of the present invention is free from side effects and can be used as an agent for the prophylaxis or treatment of Down's syndrome and the like.

Also, the apoptosis suppressor and mitochondria function ameliorator of the present invention are free from side effects and can be used as an agent for the prophylaxis or treatment of a nervous system disease and the like.

Furthermore, according to the screening method of the present invention, it is possible to screen an agent for the prophylaxis or treatment of a nervous system disease which has an excellent effect, and which is free from side effects.

The invention claimed is:

1. A method for the treatment of diseases or symptoms associated with mitochondria functional abnormalities, which comprises administering a compound to a mammal in need thereof represented by the formula (I):

wherein $R^1$ is an optionally substituted heterocyclic group;
A is an optionally substituted hydroxy group or an optionally esterified or amidated carboxyl group;
B is an optionally substituted aromatic group;
X is an oxygen atom or a sulfur atom; and
Y is a divalent hydrocarbon group,
a salt thereof or a prodrug thereof, and
wherein the diseases or symptoms associated with mitochondria functional abnormalities are pigmentary degeneration of retina, alcoholic hepatitis or sideroblastic anemia.

2. The method of claim 1, wherein $R^1$ is an optionally substituted 5-membered nitrogen-containing aromatic heterocyclic group.

3. The method of claim 1, wherein $R^1$ is an optionally substituted imidazolyl group.

4. The method of claim 1, wherein A is an optionally substituted hydroxy group.

5. The method of claim 1, wherein B is an optionally substituted phenyl group.

6. The method of claim 1, wherein X is an oxygen atom.

7. The method of claim 1, wherein Y is a divalent aliphatic hydrocarbon group.

8. The method of claim 1, wherein the compound represented by the formula (I) is 4-(4-chlorophenyl)-2-(2-methyl-1-imidazolyl)-5-[3-(2-methylphenoxy)propyl]oxazole.

* * * * *